US012221657B2

United States Patent
(12) United States Patent
Mande et al.

(10) Patent No.: US 12,221,657 B2
(45) Date of Patent: Feb. 11, 2025

(54) METHOD AND SYSTEM FOR IMPROVING AMPLICON SEQUENCING BASED TAXONOMIC RESOLUTION OF MICROBIAL COMMUNITIES

(71) Applicant: Tata Consultancy Services Limited, Mumbai (IN)

(72) Inventors: Sharmila Shekhar Mande, Pune (IN); Anirban Dutta, Pune (IN); Nishal Kumar Pinna, Pune (IN); Mohammed Monzoorul Haque, Pune (IN)

(73) Assignee: Tata Consultancy Services Limited, Mumbai (IN)

(*) Notice: Subject to any disclaimer, the term of this patent is extended or adjusted under 35 U.S.C. 154(b) by 764 days.

(21) Appl. No.: 16/537,133

(22) Filed: Aug. 9, 2019

(65) Prior Publication Data

US 2020/0115766 A1 Apr. 16, 2020

(30) Foreign Application Priority Data

Aug. 10, 2018 (IN) ............................ 201821030219

(51) Int. Cl.

| | |
|---|---|
| ***C12Q 1/6888*** | (2018.01) |
| ***C12N 15/10*** | (2006.01) |
| ***C12Q 1/6869*** | (2018.01) |
| ***G16B 10/00*** | (2019.01) |
| ***G16B 30/00*** | (2019.01) |
| ***G16B 40/10*** | (2019.01) |

(52) U.S. Cl.

CPC ....... *C12Q 1/6888* (2013.01); *C12N 15/1003* (2013.01); *C12Q 1/6869* (2013.01); *G16B 10/00* (2019.02); *G16B 30/00* (2019.02); *G16B 40/10* (2019.02)

(58) Field of Classification Search

CPC ......... G16B 10/00; G16B 40/10; G16B 30/00

See application file for complete search history.

(56) References Cited

U.S. PATENT DOCUMENTS

2017/0183724 A1 6/2017 Burke et al.

OTHER PUBLICATIONS

Fuks et al., Combining 16S rRNA gene variable regions enables high-resolution microbial community profiling, 2018, Microbiome, 6:17, p. 1-13 (Year: 2018).*

Barb et al., Development of an Analysis Pipeline Characterizing Multiple Hypervariable Regions of 16S rRNA Using Mock Samples, 2016, PLOS ONE, p. 1-16 (Year: 2016).*

Hugerth et al., Analysing Microbial Community Composition through Amplicon Sequencing: From Sampling to Hypothesis Testing, 2017, frontiers in Microbiology, p. 1-22 (Year: 2017).*

Huse et al., A Core Human Microbiome as viewed through 16S rRNA sequence clusters, 2012, PLoS one, p. 1-12 (Year: 2012).*

Ju et al. (Experimental Design and Bioinformatics Analysis for the Application of Metagenomics in Environmental Sciences and Biotechnology, 2015, Environ. Sci. Technol., 49, p. 12628-12640 (Year: 2015).*

Ali et al., Current Nucleic Acid Extraction Methods and Their Implications to Point-of-Care Diagnostics, 2017, BioMed Research International, p. 1-12 (Year: 2017).*

Milanese, A. et al. (2019). "Microbial abundance, activity and population genomic profiling with mOTUs2," *Nature Communications*, vol. 10, No. 1014; pp. 1-11.

Callahan, B. et al. (2019). "High-throughput amplicon sequencing of the full-length 16S rRNA gene with single-nucleotide resoluation," *Nucleic Acids Research*; pp. 1-12.

Ramazzotti, M. et al. (Nov. 2015). "riboFrame: An Improved Method for Microbial Taxonomy Profiling from Non-Targeted Metagenomics," *Frontiers in Genetics*, vol. 6, No. 329, pp. 1-12.

* cited by examiner

*Primary Examiner* — Kaitlyn L Minchella

(74) *Attorney, Agent, or Firm* — Finnegan, Henderson, Farabow, Garrett & Dunner, LLP

(57) ABSTRACT

The taxonomic resolution obtained with conventional sequencing methods like Sanger (longer read lengths) takes a huge amount of time. While, NGS technologies (shorter read lengths) involves a lot of cost in sequencing. In addition to that the accuracy and depth of taxonomic classification is also less. A method and system for improving accuracy of amplicon sequencing based taxonomic profiling of microbial communities has been provided. The proposed strategy relies on obtaining taxonomic abundance profiles of a microbial community from two paired-end sequencing experiments, each of which targets different pair-wise combinations of non-contiguous (or contiguous) V-regions. The two taxonomic profiles are then combined based on (pre-estimated) accuracies of the individual V-regions (targeted in the experiments) in resolving each of the taxonomic groups under consideration.

4 Claims, 12 Drawing Sheets

Specification includes a Sequence Listing.

| Target combination of V-regions | Set of available primers suitable for targeting the given combination | Forward primer sequence (5'-3') | Forward primer SEQ ID No. | Reverse primer sequence (5'-3' | Reverse primer SEQ ID NO. | No. of 16S sequences the forward primer is specific to (out of 84,711 full-length sequences from RDP) | No. of 16S sequences the reverse primer is specific to (out of 84,711 full-length sequences from RDP) | Overlap of read length (%) compared to HMM based extraction of V-region combinations |
|---|---|---|---|---|---|---|---|---|
| V1+V4 | 68F - 798R | TNANACATGCAAGTCGRRCG | 1 | AGGGTATCTAATCCT | 4 | 80679 | 84453 | 77.60 |
| V1+V3 | 68F - U529R | TNANACATGCAAGTCGRRCG | 1 | ACCGCGGCKGCTGGC | 5 | 80679 | 84247 | 91.20 |
| V1+V8 | 68F - 1401R | TNANACATGCAAGTCGRRCG | 1 | CGGTGTGTACAAGACCC | 6 | 80679 | 84345 | 81.56 |
| V1+V7 | 68F - GM12R | TNANACATGCAAGTCGRRCG | 1 | CGTCATCCMCACCTTCCTC | 7 | 80679 | 81250 | 88.60 |
| V1+V6 | 68F - 1061R | TNANACATGCAAGTCGRRCG | 1 | CRRCACGAGCTGACGAC | 8 | 80679 | 83575 | 89.20 |
| V1+V5 | 68F - 908R | TNANACATGCAAGTCGRRCG | 1 | CGTCAATTCMTTTGAGTT | 9 | 80679 | 84089 | 90.60 |
| V1+V9 | 68F - 1407R | TNANACATGCAAGTCGRRCG | 1 | GACGGGCGGTGTGTRC | 10 | 80679 | 84259 | 76.18 |
| V1V2* | 68F - 338R | TNANACATGCAAGTCGRRCG | 1 | TGCTGCCTCCCGTAGGAGT | 11 | 80679 | 83986 | 79.80 |
| V2+V4 | pBR-V1.ASF - 798R | AGTGGCGGACGGGTGAGTAA | 2 | AGGGTATCTAATCCT | 4 | 80875 | 84453 | 82.88 |
| V2+V8 | pBR-V1.ASF - 1401R | AGTGGCGGACGGGTGAGTAA | 2 | CGGTGTGTACAAGACCC | 6 | 80875 | 84345 | 86.84 |
| V2+V6 | pBR-V1.ASF - 1061R | AGTGGCGGACGGGTGAGTAA | 2 | CRRCACGAGCTGACGAC | 8 | 80875 | 83575 | 94.48 |
| V2+V7 | pBR-V1.ASF - GM12R | AGTGGCGGACGGGTGAGTAA | 2 | CGTCATCCMCACCTTCCTC | 7 | 80875 | 81250 | 93.88 |
| V2V3* | pBR-V1.ASF - U529R | AGTGGCGGACGGGTGAGTAA | 2 | ACCGCGGCKGCTGGC | 5 | 80875 | 84247 | 96.48 |
| V2+V9 | pBR-V1.ASF - 1407R | AGTGGCGGACGGGTGAGTAA | 2 | GACGGGCGGTGTGTRC | 10 | 80875 | 84259 | 81.46 |
| V2+V5 | pBR-V1.ASF - 908R | AGTGGCGGACGGGTGAGTAA | 2 | CGTCAATTCMTTTGAGTT | 9 | 80875 | 84089 | 95.88 |
| V3+V8 | 347F - 1401R | GGAGGCAGCAGTRRGGAAT | 3 | CGGTGTGTACAAGACCC | 6 | 83812 | 84345 | 87.56 |
| V3+V7 | 347F - GM12R | GGAGGCAGCAGTRRGGAAT | 3 | CGTCATCCMCACCTTCCTC | 7 | 83812 | 81250 | 94.60 |
| V3+V6 | 347F - 1061R | GGAGGCAGCAGTRRGGAAT | 3 | CRRCACGAGCTGACGAC | 8 | 83812 | 83575 | 95.20 |
| V3+V9 | 347F - 1407R | GGAGGCAGCAGTRRGGAAT | 3 | GACGGGCGGTGTGTRC | 10 | 83812 | 84259 | 82.17 |
| V3+V5 | 347F - 908R | GGAGGCAGCAGTRRGGAAT | 3 | CGTCAATTCMTTTGAGTT | 9 | 83812 | 84089 | 96.60 |

* contiguous combination

Fig. 10

METHOD AND SYSTEM FOR IMPROVING AMPLICON SEQUENCING BASED TAXONOMIC RESOLUTION OF MICROBIAL COMMUNITIES

PRIORITY CLAIM

This U.S. patent application claims priority under 35 U.S.C. § 119 to Indian Application No. 201821030219, filed on Aug. 10, 2018. The entire contents of the aforementioned application are incorporated herein by reference.

REFERENCE TO SEQUENCE LISTING SUBMITTED ELECTRONICALLY

An official copy of the sequence listing is submitted electronically via EFS-WEB as an ASCII formatted sequence listing with a file named 16537133-sequence-listing.txt, having a size of 2.69 KB. The sequence listing contained in this ASCII formatted document is part of the specification and is herein incorporated by reference in its entirety.

TECHNICAL FIELD

The embodiments herein generally relates to the field of taxonomic profiling of microbial communities. More particularly, but not specifically, the invention provides a system and method for improving amplicon sequencing based taxonomic profiling or resolution of microbial communities.

BACKGROUND

Sequencing of 16S rRNA genes is a standard protocol for taxonomic characterization of bacterial species. Sanger sequencing has been conventionally used for obtaining “full-length” 16S rRNA gene sequences of individual bacterium. Next generation sequencing (NGS) technologies have enabled probing of microbial diversity in different environmental niches with unprecedented sequencing depth. Sequencing of such regions (encompassing one or more variable regions or V-regions) has been utilized in microbiome studies for obtaining taxonomic assignments for bacterial groups present in the studied environment. However, due to read-length limitations of popular NGS technologies, 16S amplicon sequencing based microbiome studies rely on targeting short stretches of the 16S rRNA gene encompassing a selection of variable (V) regions. In most cases such a short stretch constitutes a single V-region or a couple of V-regions placed adjacent to each other on the 16S rRNA gene. Given that different V-regions have different resolving ability with respect to various taxonomic groups, selecting the optimal V-region (or a combination thereof) remains one challenge.

Furthermore, NGS technologies although enable sequencing in ultrahigh-throughput mode, they are limited with respect to read-lengths. These technologies are currently capable of yielding short sequences (referred to as reads). Due to the mentioned limitations of read-length, 16S rRNA amplicon-based microbiome studies currently rely on sequencing short stretches within the span of the 16S rRNA gene. These short stretches encompass a selection of variable (V) regions. In most cases, the said short stretch constitutes a single V-region (~150-250 base pairs in length) or a couple of V-regions placed adjacent to each other on the 16S rRNA gene. As compared to the taxonomic resolution obtained through analysis of ‘full-length’ 16S rRNA gene sequences (~1200-1500 base pairs in length) generated using the classical Sanger sequencing technology, short reads provide limited taxonomic resolution because the limited information embedded in such short reads makes it computationally challenging to unambiguously compare and associate them with template/reference database sequences whose taxonomy is known with certainty.

Nevertheless, the relative lower cost of NGS and the throughput they achieve make them an attractive proposition. The challenge/problem is to reduce the difference/gap in taxonomic resolution obtained with conventional sequencing methods like Sanger (longer read lengths) and NGS technologies (shorter read lengths) without increasing the cost of sequencing employing NGS technologies.

SUMMARY

Embodiments of the present disclosure present technological improvements as solutions to one or more of the above-mentioned technical problems recognized by the inventors in conventional systems. For example, in one embodiment, a system for improving amplicon based taxonomic resolution of microbial community. The system comprises a sample collection module, an input module, a DNA extraction module, a sequence, a first microbial abundance profile generation module, a second microbial abundance profile generation module, one or more hardware processors and a memory. The memory further comprises a computation table generation module and a combined microbial abundance profile generation module. The sample collection module collects a biological sample from environment. The input module obtains a first subsample and a second subsample from the biological sample. The DNA extraction module extracts microbial DNA from the first subsample and the second subsample. The sequencer sequences the extracted microbial DNA from the first subsample to get DNA sequence data, wherein the DNA sequence data comprises of a plurality of pairs of sequence fragments, and wherein each pair of the plurality of pairs of sequence fragments is generated through paired-end sequencing of an amplicon that comprises a first combination of informative regions within the amplicon, and wherein the said informative regions contain phylogenetically relevant information. The sequencer also sequences the extracted DNA from the second subsample to get DNA sequence data, wherein the DNA sequence data comprises of a plurality of pairs of sequence fragments, wherein each pair of the plurality of pairs of sequence fragments is generated through paired-end sequencing of the amplicon that comprises a second combination of informative regions within the amplicon, wherein the second combination of informative regions are different from the first combination of informative regions, and wherein the amplicon sequencing experiment targets a phylogenetic marker gene. The first microbial abundance profile generation module generated a microbial taxonomic abundance profile of the first sequenced subsample by employing a taxonomic classification method, wherein the taxonomic classification method utilizing phylogenetically relevant information corresponding to the first combination of informative regions, wherein the microbial taxonomic abundance profile comprises of abundance values corresponding to one or more pair of sequence fragments comprising the first combination of informative regions classified into a plurality of taxonomic groups. The second microbial abundance profile generation module generates a microbial taxonomic abundance profile of the second sequenced subsample by employing the taxonomic classification method, wherein the taxonomic classification method utilizing phylogenetically relevant information corresponding to the second combination of informative regions, wherein the microbial taxonomic abundance profile comprises of abundance values corresponding to one or more pair of sequence fragments comprising the second combination of informative regions classified into the plurality of taxonomic groups. The computation table generation module pre-computes taxonomic classification accuracies for all different possible combinations of informative regions for microbes belonging to the plurality of taxonomic groups, wherein the pre-computing is based on marker gene sequences of known taxonomic origin present in existing sequence databases, to generate a computation table. The combined microbial abundance profile generation module combines the microbial taxonomic abundance profiles of the first and the second sequenced subsample based on the computation table to generate a combined microbial taxonomic abundance profile, wherein the combined microbial taxonomic abundance profile has a refined abundance value and has improved taxonomic classification accuracy as compared to the microbial taxonomic abundance profiles obtained individually for the first and the second subsample, or as compared to a microbial taxonomic abundance profile obtained for the entire biological sample or any other subsample of a biological sample using amplicon sequencing targeting any of the combinations of informative regions in the phylogenetic marker gene.

In another aspect the embodiment here provides a method for improving accuracy of taxonomic profiling of a microbial community based on amplicon sequencing. Initially, a biological sample is collected from environment. A first subsample and a second subsample is then obtained from the biological sample. In the next step, microbial DNA is extracted from the first subsample and the second subsample. Later, The extracted microbial DNA from the first subsample is sequenced using a sequencer to get DNA sequence data, wherein the DNA sequence data comprises of a plurality of pairs of sequence fragments, and wherein each pair of the plurality of pairs of sequence fragments is generated through paired-end sequencing of an amplicon that comprises a first combination of informative regions within the amplicon, and wherein the said informative regions contain phylogenetically relevant information. Similarly, the extracted DNA from the second subsample is also sequenced using the sequencer to get DNA sequence data, wherein the DNA sequence data comprises of a plurality of pairs of sequence fragments, wherein each pair of the plurality of pairs of sequence fragments is generated through paired-end sequencing of the amplicon that comprises a second combination of informative regions within the amplicon, wherein the second combination of informative regions are different from the first combination of informative regions, and wherein the amplicon sequencing experiment targets a phylogenetic marker gene. In the next step, a microbial taxonomic abundance profile of the first sequenced subsample is generated by employing a taxonomic classification method, wherein the taxonomic classification method utilizing phylogenetically relevant information corresponding to the first combination of informative regions, wherein the microbial taxonomic abundance profile comprises of abundance values corresponding to one or more pair of sequence fragments comprising the first combination of informative regions classified into a plurality of taxonomic groups. Similarly, a microbial taxonomic abundance profile of the second sequenced subsample is generated by employing the taxonomic classification method, wherein the taxonomic classification method utilizing phylogenetically relevant information corresponding to the second combination of informative regions, wherein the microbial taxonomic abundance profile comprises of abundance values corresponding to one or more pair of sequence fragments comprising the second combination of informative regions classified into the plurality of taxonomic groups. In the next step, taxonomic classification accuracies are pre-computed for all different possible combinations of informative regions for microbes belonging to the plurality of taxonomic groups, wherein the pre-computing is based on marker gene sequences of known taxonomic origin present in existing sequence databases, to generate a computation table. And finally, the microbial taxonomic abundance profiles of the first and the second sequenced subsample is combined based on the computation table to generate a combined microbial taxonomic abundance profile, wherein the combined microbial taxonomic abundance profile has a refined abundance value and has improved taxonomic classification accuracy as compared to the microbial taxonomic abundance profiles obtained individually for the first and the second subsample, or as compared to a microbial taxonomic abundance profile obtained for the entire biological sample or any other subsample of a biological sample using amplicon sequencing targeting any of the combinations of informative regions in the phylogenetic marker gene.

In another aspect the embodiment here provides one or more non-transitory machine readable information storage mediums comprising one or more instructions which when executed by one or more hardware processors cause improving accuracy of taxonomic profiling of a microbial community based on amplicon sequencing. Initially, a biological sample is collected from environment. A first subsample and a second subsample is then obtained from the biological sample. In the next step, microbial DNA is extracted from the first subsample and the second subsample. Later, The extracted microbial DNA from the first subsample is sequenced using a sequencer to get DNA sequence data, wherein the DNA sequence data comprises of a plurality of pairs of sequence fragments, and wherein each pair of the plurality of pairs of sequence fragments is generated through paired-end sequencing of an amplicon that comprises a first combination of informative regions within the amplicon, and wherein the said informative regions contain phylogenetically relevant information. Similarly, the extracted DNA from the second subsample is also sequenced using the sequencer to get DNA sequence data, wherein the DNA sequence data comprises of a plurality of pairs of sequence fragments, wherein each pair of the plurality of pairs of sequence fragments is generated through paired-end sequencing of the amplicon that comprises a second combination of informative regions within the amplicon, wherein the second combination of informative regions are different from the first combination of informative regions, and wherein the amplicon sequencing experiment targets a phylogenetic marker gene. In the next step, a microbial taxonomic abundance profile of the first sequenced subsample is generated by employing a taxonomic classification method, wherein the taxonomic classification method utilizing phylogenetically relevant information corresponding to the first combination of informative regions, wherein the microbial taxonomic abundance profile comprises of abundance values corresponding to one or more pair of sequence fragments comprising the first combination of informative regions classified into a plurality of taxonomic groups. Similarly, a microbial taxonomic abundance profile of the second sequenced subsample is generated by employing the taxonomic classification method, wherein the taxonomic classification method utilizing phylogenetically relevant information corresponding to the second combination of informative regions, wherein the microbial taxonomic abundance profile comprises of abundance values corresponding to one or more pair of sequence fragments comprising the second combination of informative regions classified into the plurality of taxonomic groups. In the next step, taxonomic classification accuracies are pre-computed for all different possible combinations of informative regions for microbes belonging to the plurality of taxonomic groups, wherein the pre-computing is based on marker gene sequences of known taxonomic origin present in existing sequence databases, to generate a computation table. And finally, the microbial taxonomic abundance profiles of the first and the second sequenced subsample is combined based on the computation table to generate a combined microbial taxonomic abundance profile, wherein the combined microbial taxonomic abundance profile has a refined abundance value and has improved taxonomic classification accuracy as compared to the microbial taxonomic abundance profiles obtained individually for the first and the second subsample, or as compared to a microbial taxonomic abundance profile obtained for the entire biological sample or any other subsample of a biological sample using amplicon sequencing targeting any of the combinations of informative regions in the phylogenetic marker gene.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIG. 10 shows a comparison of paired-end reads generated in the in silico experiments (based on constant region HMMs) with respect to those which may be obtained by using different sets of primers currently available for 16S rRNA amplicon sequencing according to an embodiment of the disclosure.

DETAILED DESCRIPTION

Figure 1:
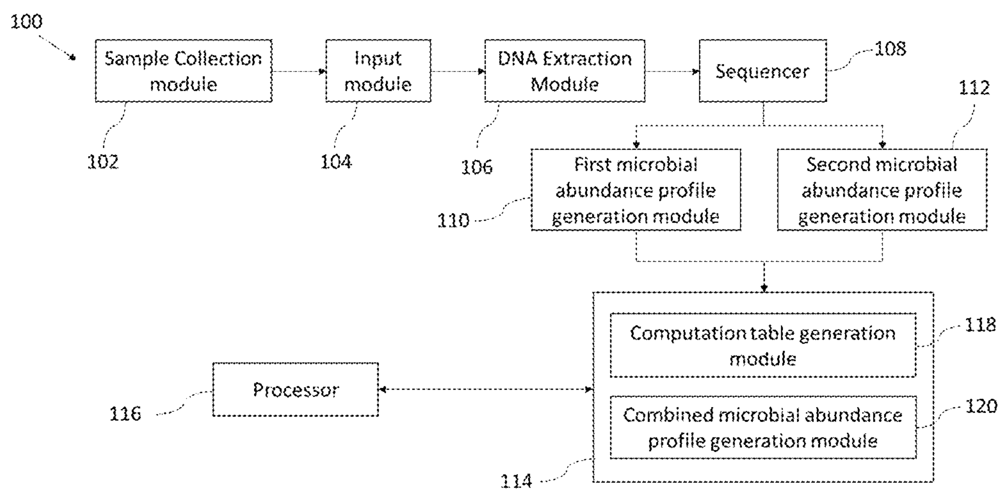
FIG. 1 illustrates a block diagram of a system for improving accuracy of amplicon based taxonomic profiling of microbial community according to an embodiment of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Referring now to the drawings, and more particularly to FIG. 1 through FIG. 10, where similar reference characters denote corresponding features consistently throughout the figures, there are shown preferred embodiments and these embodiments are described in the context of the following exemplary system and/or method.

According to an embodiment of the disclosure, a system 100 for improving accuracy of amplicon based taxonomic profiling of microbial community is shown in the block diagram of FIG. 1. More specifically, the disclosure provides a method and system for improving the resolution of 16S rRNA gene-based taxonomic profiles corresponding to microbial environments. The other amplicon gene sequences can also be used. The method and system 100 may be extended to other marker genes/genetic elements used for taxonomic classification such as the bacterial CPN60 or other Heat-Shock proteins (HSPs), and the fungal ITS elements sequences. The present disclosure provides a combinatorial strategy which involves sequencing of one pair or multiple pairs of contiguously or non-contiguously located variable regions within the 16S rRNA gene and subsequent processing and analysing the resultant sequencing data using a novel in silico combinatorial approach to improve the resolution of taxonomic profiling. The disclosure also provides increased accuracy and depth of taxonomic classification of a microbiome.

In the present disclosure, the system 100 have been explained with the help of two experiments targeting two different combinations of variable regions. Though it should be appreciated that the system 100 can also be modified to involve more than two experiments to enable targeting even more combinations which might be relevant for the biological problem.

According to an embodiment of the disclosure, the system 100 is specifically using paired end sequencing. Paired-end sequencing protocols available with some of the NGS platforms allow sequencing of a stretch of DNA from both its ends. For example, Illumina HiSeq sequencing platforms can be used for paired-end sequencing to generate up to 2×250 bp reads. To this end, appropriate primers need to be designed against a desired stretch of the 16S rRNA gene, such that the targeted V-regions (either contiguously or non-contiguously placed) reside within this stretch, and are not far from either of its boundaries. Sequencing of the amplicon generated with these primers can then be performed with a paired-end sequencing protocol, whereby these (amplified) stretches of DNA are sequenced from both ends. Two reads sequenced from each such amplicon would cover the two targeted V-regions (one from each end). Since each of the sequenced reads from any given 'pair' targets a single V-region (situated at one of the ends of the amplicon), read-length limitations do not restrict capturing the entirety of the individual V-regions. Consequently, it becomes possible to sequence almost all possible pair wise combinations of V-regions, either arranged contiguously or non-contiguously. Paired-end sequencing protocols can therefore, in principle, be employed for sequencing various pair wise combinations of contiguous or non-contiguous V-regions in a single sequencing run.

According to an embodiment of the disclosure, the system 100 further comprises a sample collection module 102, an input module 104, a DNA extraction module 106, a sequencer 108, a first microbial abundance profile generation module 110, a second microbial abundance profile generation module 112, a memory 114 and one or more hardware processor 116 as shown in the block diagram of FIG. 1. The one or more hardware processors 116 works in communication with the memory 114. The memory 114 further comprises a plurality of modules. The plurality of modules accesses the set of algorithms stored in the memory 114 to perform a certain functions. The memory 114 further comprises a computation table generation module 118 and a combined microbial abundance profile generation module 120.

According to an embodiment of the disclosure the sample collection module 102 is configured to collect a biological sample from the environment. The biological sample can be collected from various places such as gut, swab, saliva from human body or any other place outside the human body. The input module 104 is configured to obtaining a first subsample and a second subsample from the collected biological sample. In an example, the input module 104 could be same as the sample collection module 102. The sample collection module 102 and the input module 104 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite.

According to an embodiment of the disclosure, the system 100 comprises the DNA extraction module 106 and the sequencer 108. The DNA extraction module 106 is configured to extract DNA fragments from the first subsample and the second subsample using laboratory standardized protocol. The sequencer 108 is configured to sequence the extracted DNA from the first subsample and the second subsample. The sequencing for the first subsample and the second subsample is performed separately and can be performed in any order.

The sequencing of the extracted microbial DNA from the first subsample is performed using a sequencer to get DNA sequence data. The DNA sequence data comprises of a plurality of pairs of sequence fragments. Each pair of the plurality of pairs of sequence fragments is generated through paired-end sequencing of an amplicon that comprises a first combination informative regions within the amplicon, wherein the informative regions contain phylogenetically relevant information. It should be appreciated that going forward in this disclosure, the informative region can also be referred as the variable regions (V-regions) specific to 16s rRNA.

The first combination of informative regions are having contiguously or non-contiguously located informative regions.

Similarly, the sequencing of the extracted DNA from the second subsample is performed using the sequencer to get DNA sequence data. The DNA sequenced data comprises of a plurality of pairs of sequence fragments, wherein each pair of the plurality of pairs of sequence fragments is generated through paired-end sequencing of the amplicon that comprises a second combination of informative regions within the amplicon. The second combination of informative regions are having contiguously or non-contiguously located informative regions. The first combination or the second combination, can both include one or more informative regions. The second combination of informative regions are different from the first combination of informative regions. The amplicon sequencing experiment targets a phylogenetic marker gene. Though it should be appreciated that there could be overlap between the informative regions of the first combination and the second combination but they can never be exactly same. Although, the first combinations and the second combination of informative regions are always expected to be different, one of the informative regions in both combinations may be shared by both the combinations.

According to an embodiment of the disclosure, the system 100 further comprises the first microbial abundance profile generation module 110 and the second microbial abundance profile generation module 112. The first microbial abundance profile generation module 110 is configured to generate the microbial taxonomic abundance profile of the first sequenced subsample by employing a taxonomic classification method, wherein the taxonomic classification method utilizing phylogenetically relevant information corresponding to the first combination of informative regions, wherein the microbial taxonomic abundance profile comprises of abundance values corresponding to one or more pair of sequence fragments comprising the first combination of informative regions classified into a plurality of taxonomic groups. Similarly, the second microbial abundance profile generation module 112 is configured to generate a microbial abundance profile of the second sequenced subsample by employing the taxonomic classification method, wherein the taxonomic classification method utilizing phylogenetically relevant information corresponding to the second combination of informative regions, wherein the microbial abundance profile comprises of abundance values corresponding to one or more pair of sequence fragments comprising the second combination of informative regions classified into the plurality of taxonomic groups.

According to an embodiment of the disclosure, the memory 114 further comprises the computation table generation module 118. The computation table generation module 118 is configured to generate a computation table. The computation table generation module pre-compute taxonomic classification accuracies for all different possible combinations of informative regions for microbes belonging to the plurality of taxonomic groups, wherein the pre-computing is based on marker gene sequences of known taxonomic origin present in existing sequence databases, to generate a computation table. The computation table generally comprises thousands of rows and various combination of variable regions in the column. A detailed methodology and rationale employed for computing the taxonomic classification accuracies is explained in the later part of the disclosure. Due to the space and the size constraint, only a part of tables are shown below.

(a) The individual V-regions (targeted in the experiments) in resolving each of the taxonomic groups under consideration is shown in TABLE 1.

(b) Pairs of (contiguously or non-contiguously located) V-regions within the 16S rRNA gene in resolving each of the taxonomic groups under consideration is shown in TABLE 2.

TABLE 1

Taxonomic classification accuracies (in terms of number of correct assignments) obtained using different V-regions extracted from 16S rRNA sequences downloaded from RDP database. Accuracy of taxonomic assignments has been evaluated at the Genus level considering pre-annotated lineages available in RDP. The number of correct assignments that were obtained using full-length 16S rRNA genes is also indicated.

| NAME | Total Number of sequences | No. of correct assignments obtained with- Full length sequences | V1 | V2 | . . . | V9 |
|---|---|---|---|---|---|---|
| *Abiotrophia* | 4 | 4 | 0 | 3 | . . . | 0 |
| *Acaricomes* | 1 | 1 | 0 | 1 | | 0 |
| *Acetanaerobacterium* | 2 | 2 | 1 | 2 | | 0 |
| . | . | . | . . . | . | . . . | . |
| . | . | . | | . | | . |
| . | . | . | | . | | . |
| . | . | . | . . . | . | . . . | . |
| . | . | . | | . | | . |
| . | . | . | | . | | . |
| *Zymophilus* | 100 | 100 | 0 | 50 | . . . | 0 |

TABLE 2

Taxonomic classification accuracies obtained using different pair-wise combinations of V-regions (both contiguous as well as non-contiguous) evaluated with sequences downloaded from RDP database. Accuracy of taxonomic assignments has been evaluated at the species level considering the assignments obtained with full-length 16S sequences to be correct. The * symbol indicates combinations of contiguous V-regions

| NAME | V1V2* | V1 + V3 | . . . | V2V3* | . . . | V8V9* |
|---|---|---|---|---|---|---|
| Abiotrophia_defectiva_(T) | 75 | 100 | . . . | 75 | . . . | 0 |
| Acaricomes_phytoseiuli_(T) | 100 | 100 | | 100 | | 0 |
| Acetanarobacterium_elongatum_(T) | 100 | 100 | | 100 | | 100 |
| . | . | . | . . . | . | . . . | . |
| . | . | . | | . | | . |
| . | . | . | | . | | . |
| . | . | . | . . . | . | . . . | . |
| . | . | . | | . | | . |
| . | . | . | | . | | . |
| marine_bacterium_PP-203 | 100 | 100 | . . . | 100 | . . . | 100 |

According to an embodiment of the disclosure, the memory 114 further comprises the combined microbial abundance profile generation module 120. The combined microbial abundance profile generation module 120 is configured to combine the microbial taxonomic abundance profiles of the first and the second sequenced subsample based on the computation table to generate a combined microbial taxonomic abundance profile. The combined microbial taxonomic abundance profile has a refined abundance value and has improved taxonomic classification accuracy as compared to the microbial taxonomic abundance profiles obtained individually for the first and the second subsample, or as compared to a microbial taxonomic abundance profile obtained for the entire biological sample or any other subsample of a biological sample using amplicon sequencing targeting any of the combinations of informative regions in the phylogenetic marker gene.

Figure 2A:
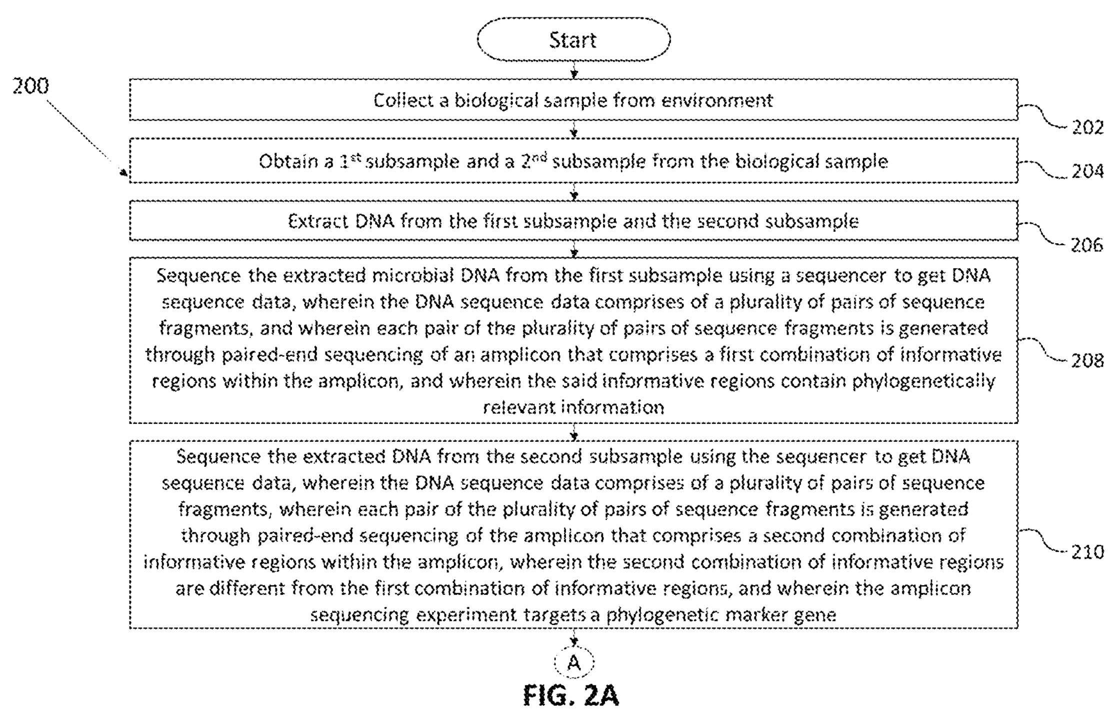
FIGS. 2A, 2B and 2C illustrate a flowchart showing the steps involved in improving accuracy of amplicon based taxonomic profiling of microbial community according to an embodiment of the present disclosure.
Figure 2B:
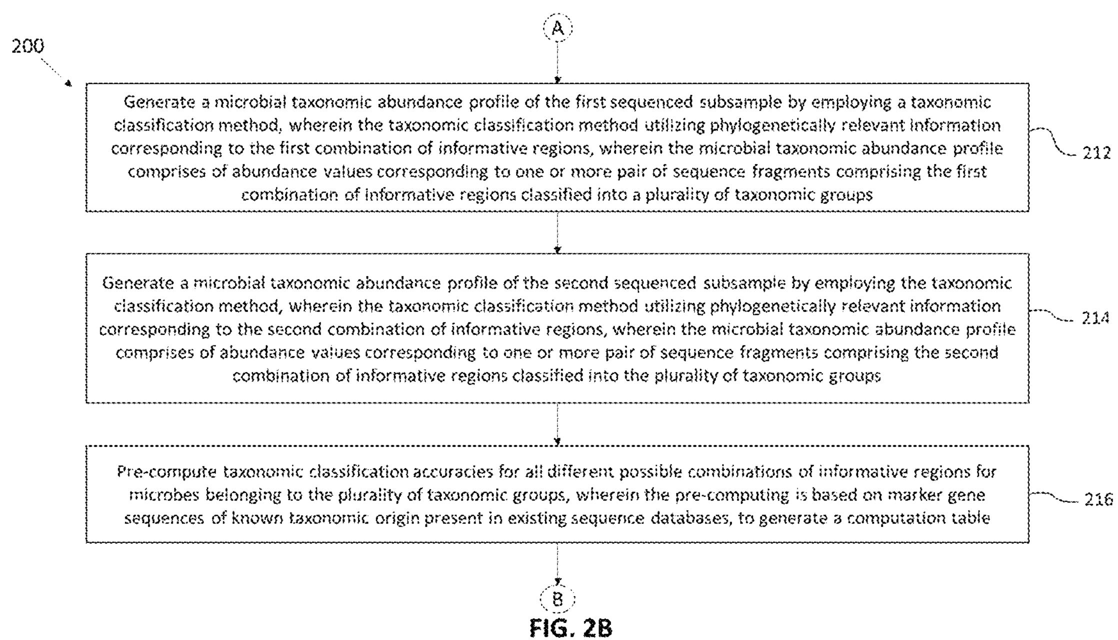
Figure 2C:
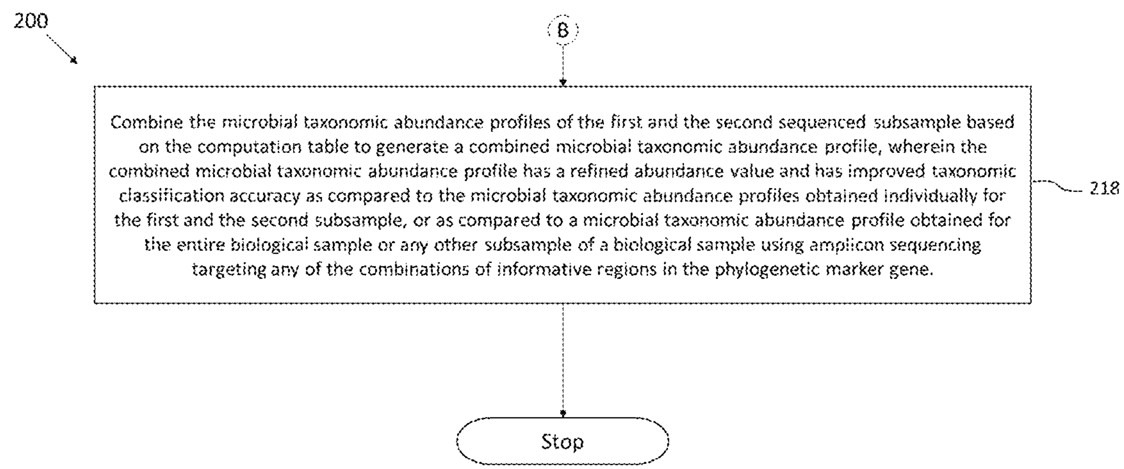

In operation, a flowchart 200 illustrating a method for improving accuracy of amplicon based taxonomic profiling of microbial community is shown in FIG. 2A-2C. Initially at step 202, the biological sample is collected from environment. The biological sample can be collected from any site not limited to human beings. At step 204, a first subsample and a second subsample is obtained from the biological sample. In the next step 206, DNA is extracted from the first subsample and the second subsample. At step 208, the extracted microbial DNA from the first subsample is sequenced using the sequencer to get DNA sequence data. The DNA sequence data comprises of a plurality of pairs of sequence fragments, wherein each pair of the plurality of pairs of sequence fragments is generated through paired-end sequencing of an amplicon that comprises a first combination informative regions within the amplicon, wherein the informative regions contain phylogenetically relevant information. Similarly, at step 210, the extracted DNA from the second subsample is sequenced using the sequencer to get DNA sequence data, wherein the DNA sequenced data comprises of a plurality of pairs of sequence fragments, wherein each pair of the plurality of pairs of sequence fragments is generated through paired-end sequencing of the amplicon that comprises a second combination of informative regions within the amplicon, wherein the second combination of informative regions are different from the first combination of informative regions, wherein the amplicon sequencing experiment targets a phylogenetic marker gene.

In the next step 212, the microbial taxonomic abundance profile of the first sequenced subsample is generated by employing a taxonomic classification method. The taxonomic classification method utilizes phylogenetically relevant information corresponding to the first combination of informative regions. The microbial taxonomic abundance profile comprises of abundance values corresponding to one or more pair of sequence fragments comprising the first combination of informative regions classified into a plurality of taxonomic groups. Similarly at step 214, the microbial abundance profile of the second sequenced subsample is generated by employing the taxonomic classification method. The taxonomic classification method utilizing phylogenetically relevant information corresponding to the second combination of informative regions. The microbial abundance profile comprises of abundance values corresponding to one or more pair of sequence fragments comprising the second combination of informative regions classified into the plurality of taxonomic groups.

At step 216, the taxonomic classification accuracies for all different possible combinations of informative regions for microbes belonging to the plurality of taxonomic groups are pre-computed. The pre-computing is based on marker gene sequences of known taxonomic origin present in existing sequence databases, to generate a computation table. At finally at step 218, the microbial abundance profiles of the first and the second sequenced subsample are combined based on the computation table to generate a combined microbial abundance profile. The combined microbial taxonomic abundance profile has a refined abundance value and has improved taxonomic classification accuracy as compared to the microbial taxonomic abundance profiles obtained individually for the first and the second subsample, or as compared to a microbial taxonomic abundance profile obtained for the entire biological sample or any other subsample of a biological sample using amplicon sequencing targeting any of the combinations of informative regions in the phylogenetic marker gene.

Figure 3:
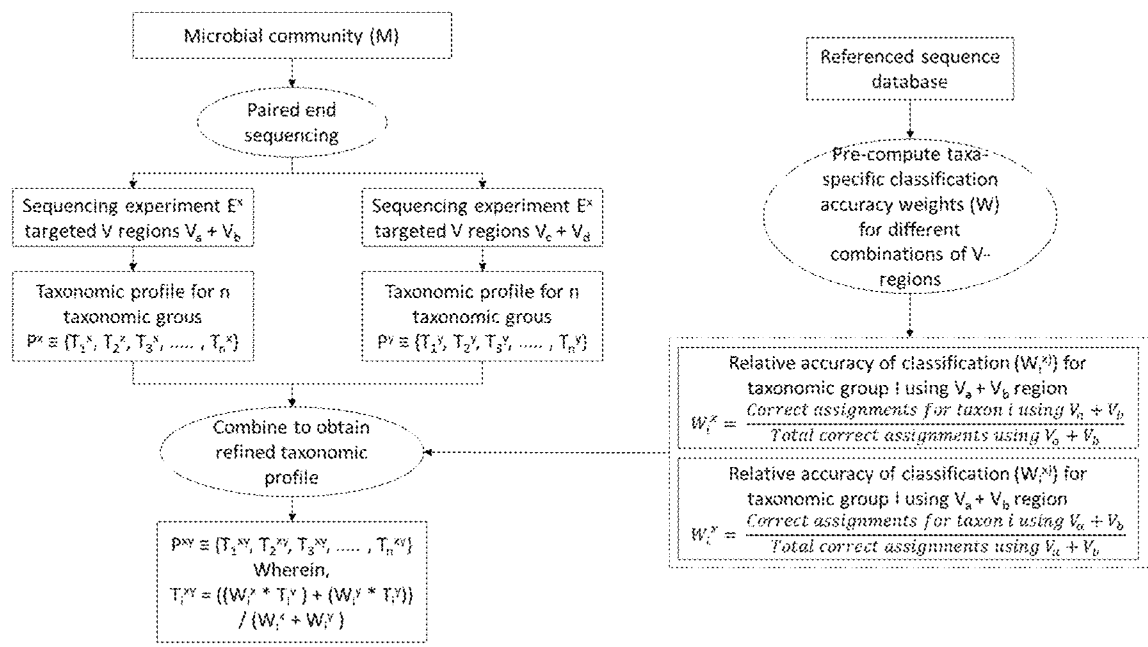
FIG. 3 is a flowchart showing combinatorial strategy for targeting multiple pair-wise combinations of non-contiguous (or contiguous) V-regions according to an embodiment of the present disclosure.

According to an embodiment of the disclosure, the system 100 can also be explained with the help experimental procedures and results. As mentioned earlier, the disclosure is using 16S rRNA as amplicon for the experimental procedures. Following are the steps involved in determining the combinatorial strategy for improving accuracy of amplicon based taxonomic profiling of microbial community as shown in the flowchart of FIG. 3.

A microbial community (M) is initially considered for metagenomic profiling by two paired-end sequencing experiments ($E^x$ and $E^y$). Each of these experiments can target 2 distinct V-regions (either arranged contiguously or non-contiguously on the 16S rRNA gene), using appropriate forward and reverse primers. In the current example, $E^x$ targets the V-region combination $V_a+V_b$, and $E^y$ targets $V_c+V_d$. For example, combinations of V-regions selected in the two experiments could be V1+V4 and V2+V6 in one scenario. Based on the taxonomic resolution efficiencies of different (combinations of) V-regions, $E^x$ and $E^y$ will generate two different taxonomic abundance profiles $P^x$ and $P^y$ respectively, each of which constitutes of estimated abundance values ($T_i$) for different taxonomic groups (i)—

$$P^x \equiv \{T_1^x, T_2^x, T_3^x, \ldots, T_n^x\} \quad \text{Equation 1}$$

$$P^y \equiv \{T_1^y, T_2^y, T_3^y, \ldots, T_n^y\} \quad \text{Equation 2}$$

Subsequently, for each of the taxonomic groups ($T_i$), a refined estimate of its abundance ($T_i^{xy}$) can be arrived at by combining the observed abundances $T_i^x$ and $T_i^y$, such that the refined abundance $T_i^{xy}$ is relatively closer to the estimate obtained with the experiment (either of $E^x$ or $E^y$) providing better classification accuracies for taxa 'i'. Calculation of the refined estimate therefore takes into consideration the taxonomic classification accuracies of the combination of V-regions that had been used for the initial set of experiments $E^x$ and $E^y$ using the following equation:

$$T_i^{xy} = \frac{\left(\frac{W_i^x}{W_i^y} * T_i^x\right) + T_i^y}{1 + \frac{W_i^x}{W_i^y}} \quad \text{Equation 3}$$

Wherein $W_i^x$ and $W_i^y$ are the relative accuracies in taxonomic classification for a particular taxonomic group 'i', obtained using the specific combination of V-regions chosen for experiments $E^x$ and $E^y$ respectively. These taxonomic classification accuracies can be calculated from the evaluation results obtained from the computation table generated in step 216 (methodology for computation of the values provided in these tables has been described in the later part of the disclosure), as a ratio of the correct assignments obtained for particular taxa using a specific combination of V-regions, and the total number of correct assignments obtained using the same V-region combination. For example, considering that the combination of $V_a+V_b$ was used in experiment $E^x$, $W_i^x$ can be calculated as:

$$W_i^x = \frac{\text{Correct assignments for taxon } i \text{ using } V_a + V_b}{\text{Total correct assignments using } V_a + V_b} \quad \text{Equation 4}$$

Similarly, $$W_i^y = \frac{\text{Correct assignments for taxon } i \text{ using } V_c + V_d}{\text{Total correct assignments using } V_c + V_d} \quad \text{Equation 5}$$

The denominator term representing "total correct assignments using $V_a+V_b$" has been introduced to capture any additional specificity of the chosen $V_a+V_b$ region toward a particular taxon 'i' in context of the overall taxonomic classification performance of $V_a+V_b$. Other simple ways of calculating the "relative accuracy in taxonomic classification" or weight ($W_i^x$), e.g., in a case wherein the denominator term is omitted, would also work fine when V-region combinations with decent classification accuracy are chosen.

It may be noted here, that in the experiment(s) using paired-end sequencing to capture two different V-regions from the 16S rRNA gene, the correspondence between the pairs of V-regions originating from the same 16S rRNA gene is retained. This allows joining the different V-regions together into a single DNA string (separated appropriately by ambiguous nucleotide characters) and providing the same as an input to taxonomic classification tools, such as the RDP classifier. However, for V-regions targeted in separate sequencing experiments, cross-experiment correspondence between the sequenced V-regions with respect to their origin 16S rRNA gene cannot be identified. This necessitates the indirect strategy of combining information obtained from different V-regions (or their combinations) for refining the taxonomic abundance estimates, as described above.

To avoid variations arising from experimental workflows and sample handling/preparations, it would be ideal to perform a single PCR step for amplicon generation, using different sets of primers appropriate for the chosen combinations of V-regions ($V_a+V_b$, and $V_c+V_d$ in the given example). However, it also needs to be mentioned here that the designed primers may have different affinities for the targeted regions on 16S rRNA genes originating from different taxonomic groups. This may again result in unequal proportions of 16S rRNA sequence fragments amplified by the different sets of primers, which would subsequently be reflected in the sequencing outcome. In such a scenario, the combination strategy needs to factor in this difference in proportions, while arriving at a refined taxonomic abundance estimate. Alternately, the experiment may target a combination of 3 V-regions (e.g. $V_a+V_b$ and $V_a+V_c$ or, $V_a+V_c$ and $V_b+V_c$), such that, either the forward primers or the reverse primers be common to the targeted combinations. This way, some equivalence in the proportions of fragments (targeting different taxonomic groups) can be maintained on account of the shared primer (for V-region) selected.

Further, it should be appreciated that if required the user can also obtain more than 2 subsamples, each targeting different V-regions. For example, there are 4 experiments—$E^a$, $E^b$, $E^c$, $E^d$ . . . then the combinatorial formula can be written as—

$$T_i^{abcd} = \frac{W_i^a * T_i^a + W_i^b * T_i^b + W_i^c * T_i^c + W_i^d * T_i^d}{W_i^a + W_i^b + W_i^c + W_i^d}$$

Wherein the values for W and T can be calculated as mentioned earlier

Evaluation Results with Novel Combinatorial Strategy

Figure 4:
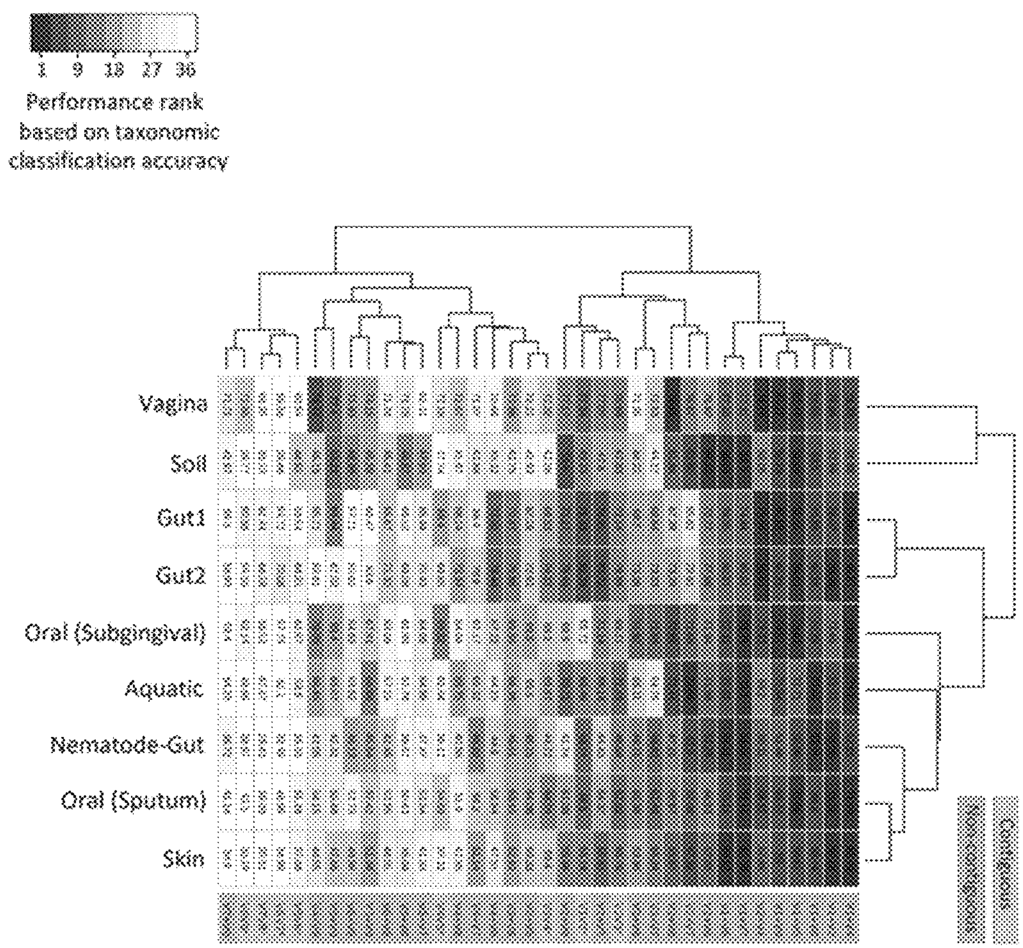
FIG. 4 shows taxonomic classification efficiency of different combinations of V-regions evaluated on nine simulated microbiome datasets mimicking different host (human) associated and/or other environmental niches according to an embodiment of the disclosure.

Considering the fact that human gut is one of the most diverse and densely populated reservoir of microbes, the utility of the combinatorial strategy was assessed with a simulated metagenomic sample (namely GUT1—method of generating the same has been described in the later part of the disclosure) that was specifically generated for this purpose (along with 7 more simulated metagenomes pertaining to different human body sites). The taxonomic classification efficiency of the V-region combinations (at the species level) was assessed on the simulated metagenome GUT1. The V-region combinations V1+V4 and V1+V5 provided highest average classification accuracies for most of the host (human) associated environmental niches along with the simulated metagenome GUT1 as shown in FIG. 4. Consequently, these V-region combinations were targeted for evaluating this combinatorial strategy wherein 5,000 sequence fragments corresponding to each of the V-region combinations (i.e. a total of 10,000 fragments) were sampled from the simulated metagenome. The results obtained with the combinatorial strategy were compared against the results obtained when each of the V-region combinations were targeted separately (with a sequencing depth of 10,000 reads in each case).

Results in Table 3 indicate that although the V1+V4 and V1+V5 regions can classify the reads with commendable accuracy, the abundance values provided for individual genera deviates from the actual (RDP) lineage by a certain extent. The combinatorial approach was observed to moderate these deviations to a significant extent, and relative abundance of individual genera ascertained by the combinatorial approach exhibited better coherence with the actual lineage. In quantitative terms, while the average deviations (from actual lineage) in relative taxonomic abundance predictions for V1+V4 and V1+V5 combination based approaches were 17.4% and 11.5% respectively, the combinatorial approach exhibited a significantly lower average deviation (6.9%) from the actual lineage. Similar improvements were also observed when this approach was tested on microbiomes pertaining to other host-associated/environmental. Given that the proposed combinatorial approach does not incur any significant additional sequencing cost and is a simple in silico extrapolation of the results obtained with standard pair-end sequencing, adoption of the same would be easy and would enable researchers to explore the taxonomic diversity of different environments with greater accuracy. While certain additional experimental costs for primers, multiplexing barcodes, additional PCR, and handling etc. are expected to be incurred to implement the proposed combinatorial strategy, the actual sequencing (reagents) cost, constituting the bulk of the total expenditure, remains the same. The additional pre-processing and handling efforts can at most be twice compared to the sample handling efforts needed for a single paired-end sequencing experiment. However, the potential benefits in terms of an improved taxonomic resolution are expected to outweigh any inhibitions arising due to the additional, but trivial, pre-processing and handling efforts.

Figure 5:
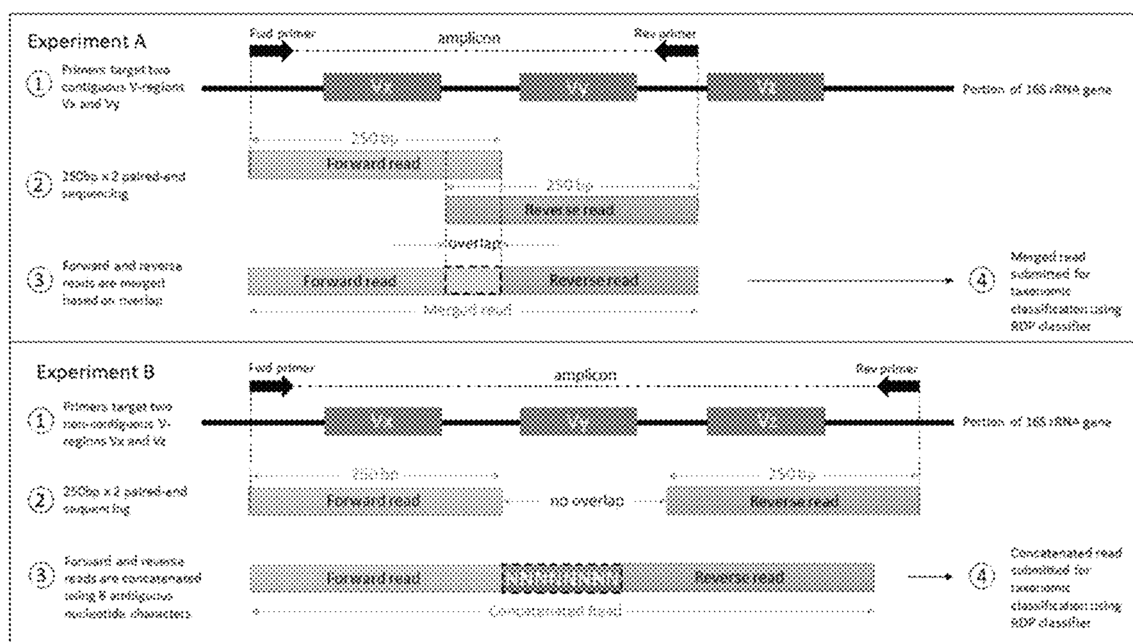
FIG. 5 depicts two amplicon sequencing experiments targeting different combinations of V-regions according to an embodiment of the disclosure.

FIG. 5 is schematic depicting two amplicon sequencing experiments targeting different combinations of V-regions. Experiment A targets two contiguous V-regions ($V_X$ and $V_Y$). The resulting paired end reads (generated through 250 bp×2 paired end sequencing of the amplicon) are merged together utilizing the overlapping region. Subsequently, the merged read is used for taxonomic classification. Similarly, experiment B targets two non-contiguously placed V regions ($V_X$ and $V_Z$). The resulting pair-end reads do not have any overlap and are concatenated together using eight ambiguous nucleotide characters (N). Subsequently, the concatenated read is used for taxonomic classification.

TABLE 3

Utility of proposed combinatorial approach in obtaining refined taxonomic profiles compared to taxonomic abundance estimates obtained with pair wise combinations of V-regions. Results in the table pertain to the simulated human gut metagenomic dataset GUT1.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Faecalibacteriumprausnitzii* | 11.17 | 12.24 | 12.25 | 10.97 |
| *Bacteroides faecis* | 10.69 | 11.97 | 11.24 | 11.26 |
| *Prevotellaamnii* | 6.73 | 0.00 | 6.72 | 7.22 |
| *Prevotellanigrescens* | 6.47 | 6.98 | 6.76 | 6.90 |
| *Megamonashypermegale* | 5.35 | 6.06 | 3.53 | 4.61 |
| *Bacteroides pyogenes* | 4.23 | 4.44 | 4.33 | 4.52 |

TABLE 3-continued

Utility of proposed combinatorial approach in obtaining refined taxonomic profiles compared to taxonomic abundance estimates obtained with pair wise combinations of V-regions. Results in the table pertain to the simulated human gut metagenomic dataset GUT1.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Bacteroides finegoldii* | 3.98 | 4.03 | 4.13 | 3.97 |
| *Alistipesputredinis* | 3.45 | 3.73 | 3.71 | 3.48 |
| *Roseburia hominis* | 2.41 | 2.70 | 2.84 | 2.59 |
| *Bacteroides nordii* | 2.18 | 2.50 | 2.26 | 2.14 |
| *Bacteroides eggerthii* | 2.15 | 2.51 | 2.24 | 2.13 |
| *Bacteroides helcogenes* | 2.09 | 2.35 | 2.13 | 2.09 |
| *Bacteroides caccae* | 2.08 | 2.30 | 2.32 | 2.29 |
| *Bacteroides massiliensis* | 2.07 | 2.10 | 2.13 | 2.00 |
| *Bacteroides coprocola* | 2.04 | 2.43 | 2.27 | 2.20 |
| *Bacteroides salyersiae* | 2.04 | 2.26 | 2.01 | 2.10 |
| *Bacteroides stercoris* | 2.03 | 1.92 | 2.50 | 2.15 |
| *Bacteroides uniformis* | 2.02 | 2.03 | 2.04 | 1.92 |
| *Bacteroides acidifaciens* | 2.01 | 2.30 | 2.00 | 2.06 |
| *Proteiniphilumacetatigenes* | 2.01 | 2.21 | 2.18 | 2.06 |
| *Bacteroides cellulosilyticus* | 1.98 | 2.16 | 0.00 | 1.95 |
| *Bacteroides intestinalis* | 1.96 | 2.02 | 2.08 | 2.01 |
| *Roseburiafaecis* | 1.74 | 1.94 | 1.91 | 1.68 |
| *Roseburia intestinalis* | 1.74 | 2.16 | 1.91 | 1.84 |
| *Parasutterellasecunda* | 1.50 | 1.74 | 1.56 | 1.38 |
| *Roseburiainulinivorans* | 1.00 | 1.00 | 1.06 | 1.10 |
| *Phascolarctobacteriumsuccinat* | 0.99 | 0.82 | 0.78 | 0.80 |
| *Parabacteroides distasonis* | 0.90 | 1.03 | 1.04 | 0.73 |
| *Parabacteroides merdae* | 0.89 | 1.07 | 0.87 | 0.90 |
| *Parasutterellaexcrementihomin* | 0.82 | 0.99 | 0.84 | 0.74 |
| *Dorealongicatena* | 0.78 | 0.32 | 0.51 | 0.32 |
| *Phascolarctobacterium faecium* | 0.74 | 0.81 | 0.83 | 0.69 |
| *Blautiaproducta* | 0.70 | 0.55 | 0.86 | 0.61 |
| *Escherichia/Shigella fergusonii* | 0.69 | 0.59 | 0.00 | 0.64 |
| *Escherichia/Shigella albertii* | 0.57 | 0.56 | 0.62 | 0.70 |
| *Escherichia/Shigella flexneri* | 0.56 | 0.00 | 0.00 | 0.00 |
| *Escherichia/Shigella* | 0.53 | 0.50 | 0.54 | 0.57 |
| *Dialisterinvisus* | 0.47 | 0.58 | 0.50 | 0.45 |
| *Megasphaeraelsdenii* | 0.46 | 0.37 | 0.47 | 0.39 |
| *Blautiaglucerasea* | 0.45 | 0.41 | 0.48 | 0.60 |
| *Blautiahydrogenotrophica* | 0.43 | 0.44 | 0.46 | 0.51 |
| *Blautiaschinkii* | 0.43 | 0.47 | 0.54 | 0.43 |
| *Mitsuokellaialaludinii* | 0.39 | 0.40 | 0.42 | 0.34 |
| *Collinsellaaerofaciens* | 0.34 | 0.37 | 0.42 | 0.36 |
| *Bifidobacterium longum* | 0.32 | 0.40 | 0.37 | 0.36 |
| *Bifidobacterium animalis* | 0.32 | 0.25 | 0.32 | 0.29 |
| *Ruminococcusflavefaciens* | 0.30 | 0.21 | 0.25 | 0.17 |
| *Blautiahansenii* | 0.28 | 0.33 | 0.30 | 0.32 |
| *Megasphaera* sp. NMBHI-10 | 0.28 | 0.22 | 0.19 | 0.16 |
| *Klebsiella pneumoniae* | 0.25 | 0.21 | 0.29 | 0.27 |
| Cumulate Percentage Deviation from abundance estimated using full-length 16S sequences | — | 17.40 | 11.47 | 6.85 |

Similarly, Table 4, Table 5, Table 6, Table 7, Table 8, Table 9, Table 10 and Table 11 show the results of other simulated microbiome of GUT2, Sputum (oral), sub-gingival (oral), skin, soil, aquatic, vagina and nematode gut respectively. The same has also been shown in FIG. 4.

TABLE 4

Utility of proposed combinatorial approach in obtaining refined taxonomic profiles compared to taxonomic abundance estimates obtained with pair-wise combinations of V-regions. Results in the table pertain to the simulated human gut microbiome dataset Gut2.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Bacteroides faecis* (T) | 13.23 | 13.23 | 13.31 | 13.54 |
| *Alistipes putredinis* (T) | 9.14 | 9.24 | 9.85 | 9.54 |
| *Faecalibacterium prausnitzii* (T) | 8.42 | 8.67 | 8.64 | 8.18 |
| *Bacteroides pyogenes* (T) | 5.24 | 4.99 | 5.51 | 4.94 |
| *Bacteroides finegoldii* (T) | 4.89 | 4.93 | 5.33 | 4.72 |
| *Parabacteroides merdae* (T) | 3.57 | 3.81 | 3.70 | 3.38 |
| *Parabacteroides distasonis* (T) | 3.23 | 3.19 | 3.36 | 3.41 |
| *Oscillibacter valericigenes* (T) | 2.95 | 3.23 | 3.01 | 3.03 |
| *Bacteroides acidifaciens* (T) | 2.81 | 2.71 | 2.88 | 2.88 |
| *Bacteroides salyersiae* (T) | 2.72 | 2.85 | 2.98 | 2.60 |
| *Bacteroides coprocola* (T) | 2.65 | 2.29 | 2.82 | 2.79 |
| *Bacteroides massiliensis* (T) | 2.64 | 2.69 | 2.94 | 2.79 |
| *Bacteroides intestinalis* (T) | 2.63 | 2.60 | 2.77 | 2.35 |
| *Bacteroides uniformis* (T) | 2.62 | 2.89 | 2.74 | 2.69 |
| *Bacteroides stercoris* (T) | 2.59 | 2.53 | 2.60 | 2.88 |
| *Bacteroides cellulosilyticus* (T) | 2.58 | 2.45 | 0.00 | 2.60 |
| *Bacteroides eggerthii* (T) | 2.53 | 2.71 | 2.67 | 2.62 |
| *Bacteroides caccae* (T) | 2.50 | 2.74 | 2.72 | 2.69 |
| *Proteiniphilum acetatgenes* (T) | 2.48 | 2.70 | 2.20 | 2.81 |
| *Bacteroides helcogenes* (T) | 2.47 | 2.74 | 2.41 | 2.37 |
| *Bacteroides nordii* (T) | 2.41 | 2.68 | 2.51 | 2.46 |
| *Ruminococcus flavefaciens* (T) | 1.51 | 1.00 | 1.29 | 1.08 |
| *Ruminococcus albus* (T) | 1.45 | 1.24 | 1.30 | 1.26 |
| *Roseburia hominis* (T) | 1.08 | 1.11 | 1.10 | 1.12 |
| *Odoribacter laneus* (T) | 0.93 | 0.80 | 1.05 | 0.94 |
| *Roseburia intestinalis* (T) | 0.88 | 0.81 | 0.95 | 0.78 |
| *Parasutterella secunda* (T) | 0.86 | 1.08 | 0.95 | 0.76 |
| *Phascolarctobacterium succinatutens* YIT 12067 | 0.81 | 0.73 | 0.55 | 0.72 |
| *Roseburia faecis* (T) | 0.79 | 0.74 | 0.73 | 0.75 |
| *Dialister invisus* (T) | 0.68 | 0.72 | 0.66 | 0.71 |
| *Phascolarctobacterium faecium* (T) | 0.60 | 0.63 | 0.62 | 0.54 |
| *Prevotella amnii* (T) | 0.55 | 0.00 | 0.74 | 0.58 |
| *Prevotella nigrescens* (T) | 0.54 | 0.57 | 0.51 | 0.52 |
| *Roseburia inulinivorans* (T) | 0.49 | 0.64 | 0.48 | 0.55 |
| *Flavonifractor plautii* (T) | 0.46 | 0.45 | 0.41 | 0.55 |
| *Blautia producta* (T) | 0.46 | 0.23 | 0.47 | 0.46 |
| *Coprococcus catus* (T) | 0.42 | 0.45 | 0.39 | 0.50 |
| *Parasutterella excrementihominis* (T) | 0.40 | 0.41 | 0.36 | 0.37 |
| *Dialister pneumosintes* (T) | 0.38 | 0.39 | 0.47 | 0.33 |
| *Dorea longicatena* (T) | 0.38 | 0.14 | 0.09 | 0.12 |
| *Ruminococcus bromii* (T) | 0.28 | 0.23 | 0.15 | 0.26 |
| *Blautia hydrogenotrophica* (T) | 0.25 | 0.24 | 0.27 | 0.27 |
| *Coprococcus eutactus* (T) | 0.24 | 0.28 | 0.25 | 0.24 |
| *Blautia glucerasea* (T) | 0.22 | 0.24 | 0.22 | 0.22 |
| *Blautia schinkii* (T) | 0.21 | 0.22 | 0.25 | 0.16 |
| *Blautia wexlerae* (T) | 0.21 | 0.19 | 0.17 | 0.26 |
| *Butyriccoccus pullicaecorum* (T) | 0.19 | 0.18 | 0.20 | 0.24 |
| *Butyricmonas synergistica* (T) | 0.15 | 0.15 | 0.10 | 0.20 |
| *Blautia hansenii* (T) | 0.14 | 0.11 | 0.19 | 0.12 |
| *Ruminococcus faecis* (T) | 0.11 | 0.11 | 0.13 | 0.11 |
| Cumulated Percentage Deviation from abundance estimated using full-length 16S sequences | — | 6.32 | 8.64 | 5.67 |

TABLE 5

Utility of proposed combinatorial approach in obtaining refined taxonomic profiles compared to taxonomic abundance estimates obtained with pair-wise combinations of V-regions. Results in the table pertain to the simulated human gut microbiome dataset Sputum.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Prevotella amnii* (T) | 8.05 | 0.00 | 9.60 | 8.81 |
| *Prevotella nigrescens* (T) | 7.85 | 9.65 | 9.08 | 7.95 |
| *Streptococcus salivarius* (T) | 7.64 | 8.48 | 8.91 | 8.24 |
| *Streptococcus suis* (T) | 6.19 | 7.29 | 7.15 | 6.59 |
| *Granulicatella adiacens* (T) | 5.81 | 6.72 | 3.32 | 5.43 |
| *Fusobacterium nucleatum* (T) | 4.59 | 4.59 | 4.82 | 4.34 |
| *Streptococcus agalactiae* (T) | 4.22 | 5.14 | 4.83 | 4.73 |
| *Staphylococcus aureus* (T) | 4.03 | 4.64 | 4.83 | 4.35 |
| *Streptococcus pyogenes* (T) | 3.39 | 3.52 | 0.19 | 3.27 |
| *Neisseria meningitidis* | 2.84 | 2.72 | 1.58 | 2.05 |
| *Streptococcus gallolyticus* (T) | 2.31 | 2.65 | 2.62 | 2.66 |
| *Rothia dentocariosa* (T) | 2.20 | 2.49 | 2.67 | 2.33 |
| *Streptococcus dysgalactiae* (T) | 2.04 | 2.40 | 2.42 | 2.35 |
| *Veillonella parvula* (T) | 2.04 | 1.98 | 2.24 | 2.23 |
| *Propionibacterium acnes* (T) | 1.92 | 2.07 | 2.12 | 2.41 |
| *Rothia aeria* (T) | 1.90 | 2.44 | 2.45 | 2.19 |
| *Veillonella tobetsuensis* (T) | 1.90 | 2.12 | 2.35 | 1.92 |
| *Streptococcus pneumoniae* (T) | 1.74 | 0.72 | 0.88 | 0.89 |
| *Rothia mucilaginosa* (T) | 1.65 | 1.95 | 1.20 | 1.47 |
| *Haemophilus aegyptius* (T) | 1.58 | 1.91 | 1.61 | 1.61 |
| *Gemella sanguinis* (T) | 1.50 | 1.59 | 1.61 | 1.61 |
| *Gemella haemolysans* (T) | 1.43 | 1.73 | 1.55 | 1.37 |
| *Actinomyces neuii* (T) | 1.39 | 1.60 | 1.86 | 1.68 |
| *Gemella bergeri* (T) | 1.38 | 1.32 | 1.53 | 1.76 |
| *Gemella morbillorum* (T) | 1.37 | 1.09 | 1.23 | 1.22 |
| *Dolosigranulum pigrum* (T) | 1.36 | 1.51 | 1.52 | 1.71 |
| *Veillonella criceti* (T) | 1.35 | 0.79 | 0.68 | 0.68 |
| *Streptococcus egui* (T) | 1.34 | 1.71 | 1.64 | 1.29 |
| *Streptococcus infantarius* (T) | 1.15 | 1.31 | 1.28 | 1.08 |
| *Pelomonas saccharophila* (T) | 1.10 | 0.28 | 0.11 | 0.38 |
| *Rothia endophytica* | 0.93 | 0.93 | 0.96 | 0.99 |
| *Staphylococcus warneri* (T) | 0.91 | 1.12 | 0.90 | 0.93 |
| *Acinetobacter baumannii* (T) | 0.85 | 0.93 | 0.90 | 0.94 |
| *Veillonella atypica* (T) | 0.77 | 0.00 | 0.00 | 0.00 |
| *Rothia amarae* (T) | 0.71 | 1.01 | 0.90 | 0.62 |
| *Veillonella denticariosi* (T) | 0.71 | 1.01 | 0.36 | 0.57 |
| *Veillonella ratti* (T) | 0.69 | 0.36 | 0.00 | 0.11 |
| *Anoxybacillus rupiensis* (T) | 0.68 | 0.87 | 0.85 | 0.74 |
| *Actinomyces coleocanis* (T) | 0.68 | 0.70 | 0.82 | 0.77 |
| *Staphylococcus cohnii* (T) | 0.60 | 0.67 | 0.57 | 0.50 |
| *Streptococcus constellatus* (T) | 0.59 | 0.83 | 0.66 | 0.60 |
| *Peptostreptococcus russellii* (T) | 0.55 | 0.59 | 0.76 | 0.62 |
| *Solobacterium moorei* (T) | 0.54 | 0.65 | 0.68 | 0.57 |
| *Staphylococcus hominis* (T) | 0.54 | 0.59 | 0.63 | 0.54 |
| *Parvimonas micra* (T) | 0.54 | 0.65 | 0.73 | 0.54 |
| *Stenotrophomonas rhizophila* (T) | 0.53 | 0.53 | 0.46 | 0.58 |
| *Streptococcus iniae* (T) | 0.50 | 0.62 | 0.54 | 0.39 |
| *Gemella palaticanis* (T) | 0.49 | 0.59 | 0.43 | 0.66 |
| *Peptostreptococcus anaerobius* (T) | 0.46 | 0.54 | 0.65 | 0.52 |
| *Streptococcus pseudoporcinus* (T) | 0.46 | 0.37 | 0.32 | 0.20 |
| Cumulated Percentage Deviation from abundance estimated using full-length 16S sequences | — | 24.30 | 24.35 | 12.64 |

TABLE 6

Utility of proposed combinatorial approach in obtaining refined taxonomic profiles compared to taxonomic abundance estimates obtained with pair-wise combinations of V-regions. Results in the table pertain to the simulated human gut microbiome dataset Sub-gingival.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Fusobacterium nucleatum* (T) | 19.16 | 21.85 | 19.74 | 19.69 |
| *Prevotella nigrescens* (T) | 11.17 | 12.88 | 12.66 | 12.57 |
| *Prevotella amnii* (T) | 10.27 | 0.00 | 11.42 | 10.43 |
| *Parvimonas micra* (T) | 4.41 | 5.50 | 5.13 | 4.83 |
| *Streptococcus salivarius* (T) | 4.40 | 5.36 | 5.07 | 4.52 |
| *Streptococcus suis* (T) | 3.63 | 4.47 | 3.80 | 4.26 |
| *Streptococcus agalactiae* (T) | 2.85 | 3.32 | 3.28 | 3.13 |
| *Streptococcus pyogenes* (T) | 2.19 | 2.68 | 0.16 | 2.40 |
| *Capnocytophaga canimorsus* (T) | 2.12 | 2.61 | 2.13 | 1.91 |
| *Granulicatella adiacens* (T) | 1.85 | 2.00 | 1.03 | 1.59 |
| *Porphyromonas crevioricanis* (T) | 1.84 | 2.36 | 1.99 | 1.84 |
| *Campylobacter lari* (T) | 1.77 | 0.42 | 0.42 | 0.60 |
| *Treponema maltophilum* (T) | 1.57 | 1.15 | 1.62 | 1.31 |
| *Acinetobacter baumannii* (T) | 1.45 | 1.66 | 1.39 | 1.37 |
| *Streptococcus gallolyticus* (T) | 1.45 | 1.87 | 1.57 | 1.81 |
| *Fusobacterium necrophorum* (T) | 1.38 | 1.68 | 1.65 | 1.56 |
| *Streptococcus dysgalactiae* (T) | 1.37 | 1.74 | 1.69 | 1.35 |
| *Neisseria meningitidis* | 1.31 | 1.50 | 0.73 | 0.96 |
| *Leptotrichia buccalis* (T) | 1.25 | 1.53 | 1.23 | 1.12 |
| *Porphyromonas somerae* (T) | 1.25 | 1.48 | 1.47 | 1.19 |
| *Enhydrobacter aerosaccus* (T) | 1.18 | 1.37 | 1.17 | 1.43 |
| *Aggregatibacter aphrophilus* (T) | 1.16 | 1.10 | 1.20 | 1.19 |
| *Actinomyces neuii* (T) | 1.13 | 1.37 | 1.23 | 1.29 |
| *Filifactor villosus* (T) | 1.11 | 1.10 | 1.29 | 1.17 |
| *Fusobacterium varium* (T) | 1.07 | 1.21 | 1.27 | 1.19 |
| *Reyranella massiliensis* | 1.07 | 1.34 | 0.97 | 1.14 |
| *Streptococcus pneumoniae* (T) | 1.07 | 0.63 | 0.54 | 0.53 |
| *Treponema lecithinolyticum* (T) | 0.97 | 1.23 | 1.00 | 1.03 |
| *Veillonella parvula* (T) | 0.94 | 0.89 | 0.94 | 0.85 |
| *Streptococcus egui* (T) | 0.90 | 0.95 | 0.97 | 0.79 |
| *Treponema amylovorum* (T) | 0.89 | 1.11 | 1.00 | 0.78 |
| *Veillonella tobetsuensis* (T) | 0.82 | 0.97 | 0.93 | 0.95 |
| *Fusobacterium mortiferum* (T) | 0.75 | 0.45 | 0.27 | 0.24 |
| *Treponema socranskii* (T) | 0.71 | 0.97 | 0.81 | 0.82 |
| *Streptococcus infantarius* (T) | 0.70 | 0.69 | 0.57 | 0.72 |
| *Porphyromonas asaccharolytica* DSM 20707 (T) | 0.69 | 0.87 | 0.76 | 0.75 |
| *Leptotrichia wadei* (T) | 0.68 | 0.90 | 0.73 | 0.65 |
| *Porphyromonas endodontalis* (T) | 0.65 | 0.00 | 0.00 | 0.00 |
| *Acinetobacter calcoaceticus* (T) | 0.64 | 0.65 | 0.45 | 0.69 |
| *Leptotrichia goodfellowii* (T) | 0.64 | 0.86 | 0.61 | 0.72 |
| *Veillonella criceti* (T) | 0.63 | 0.37 | 0.25 | 0.28 |
| *Actinomyces coleocanis* (T) | 0.60 | 0.69 | 0.76 | 0.60 |
| *Porphyromonas gulae* (T) | 0.60 | 0.00 | 0.00 | 0.00 |
| *Sphingobacterium spiritivorum* (T) | 0.57 | 0.40 | 0.52 | 0.57 |
| *Catonella morbi* (T) | 0.57 | 0.79 | 0.64 | 0.50 |
| *Porphyromonas cansulci* (T) | 0.54 | 0.60 | 0.67 | 0.53 |
| *Rothia aeria* (T) | 0.53 | 0.66 | 0.63 | 0.56 |
| *Leptotrichia hofstadii* (T) | 0.51 | 0.56 | 0.72 | 0.66 |
| *Acinetobacter lwoffii* (T) | 0.49 | 0.52 | 0.40 | 0.40 |
| *Capnocytophaga cynodegmi* (T) | 0.49 | 0.66 | 0.49 | 0.55 |
| Cumulated Percentage Deviation from abundance estimated using full-length 16S sequences | — | 29.18 | 16.17 | 11.42 |

TABLE 7

Utility of proposed combinatorial approach in obtaining refined taxonomic profiles compared to taxonomic abundance estimates obtained with pair-wise combinations of V-regions. Results in the table pertain to the simulated human gut microbiome dataset Skin.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Staphylococcus aureus* (T) | 20.21 | 22.76 | 24.06 | 22.83 |
| *Propionibacterium acnes* (T) | 11.28 | 13.11 | 13.41 | 12.33 |
| *Staphylococcus warneri* (T) | 3.81 | 4.26 | 4.43 | 4.44 |
| *Methylobacterium populi* (T) | 3.28 | 0.41 | 0.55 | 0.55 |
| *Cupriavidus taiwanensis* (T) | 2.96 | 2.70 | 2.56 | 2.66 |
| *Schlegelella thermodepolymerans* (T) | 2.92 | 3.89 | 3.68 | 3.44 |
| *Staphylococcus cohnii* (T) | 2.55 | 2.74 | 3.13 | 2.64 |
| *Staphylococcus hominis* (T) | 2.45 | 2.83 | 2.80 | 2.91 |
| *Cupriavidus basilensis* (T) | 2.40 | 2.70 | 2.87 | 2.56 |
| *Uruburuella suis* (T) | 2.39 | 2.65 | 2.84 | 2.88 |
| *Corynebacterium diphtheriae* (T) | 2.35 | 2.91 | 2.76 | 2.35 |
| *Corynebacterium glutamicum* (T) | 2.27 | 2.61 | 2.98 | 3.09 |
| *Cupriavidus respiraculi* (T) | 2.06 | 2.35 | 1.85 | 2.00 |
| *Staphylococcus sciuri* (T) | 1.88 | 2.22 | 2.09 | 1.84 |
| *Micrococcus yunnanensis* (T) | 1.55 | 0.00 | 0.00 | 0.00 |
| *Methylobacterium komagatae* (T) | 1.47 | 1.41 | 1.12 | 1.14 |
| *Streptococcus salivarius* (T) | 1.47 | 1.50 | 1.52 | 1.44 |
| *Methylobacterium goesingense* (T) | 1.45 | 1.74 | 1.57 | 1.70 |
| *Dermacoccus nishinomiyaensis* (T) | 1.38 | 1.89 | 1.54 | 1.76 |
| *Corynebacterium bovis* (T) | 1.32 | 1.50 | 1.65 | 1.53 |
| *Staphylococcus equorum* (T) | 1.28 | 1.65 | 1.46 | 1.43 |
| *Streptococcus suis* (T) | 1.26 | 1.33 | 1.59 | 1.57 |
| *Methylobacterium hispanicum* (T) | 1.23 | 0.00 | 0.00 | 0.00 |
| *Finegoldia magna* (T) | 1.20 | 1.30 | 1.37 | 1.43 |
| *Schlegelella aquatica* (T) | 1.20 | 0.00 | 1.48 | 1.92 |
| *Ralstonia syzygii* | 1.18 | 0.26 | 0.33 | 0.43 |
| *Cupriavidus pauculus* (T) | 1.13 | 1.41 | 1.30 | 1.27 |
| *Staphylococcus capitis* (T) | 1.13 | 1.28 | 1.28 | 1.31 |
| *Geobacillus stearothermophilus* (T) | 1.05 | 1.00 | 0.84 | 1.05 |
| *Wautersia numazuensis* (T) | 1.04 | 0.13 | 0.09 | 0.15 |
| *Methylobacterium mesophilicum* (T) | 0.99 | 1.09 | 0.88 | 0.78 |
| *Staphylococcus pasteuri* (T) | 0.95 | 1.09 | 1.10 | 1.45 |
| *Cupriavidus campinensis* (T) | 0.93 | 1.04 | 0.95 | 1.18 |
| *Staphylococcus carnosus* (T) | 0.93 | 0.96 | 0.66 | 0.91 |
| *Cupriavidus alkaliphilus* (T) | 0.91 | 1.06 | 0.13 | 0.84 |
| *Methylobacterium rhodesianum* (T) | 0.90 | 1.06 | 1.17 | 1.05 |
| *Methylobacterium marchantiae* (T) | 0.87 | 0.59 | 0.71 | 0.69 |
| *Lactobacillus plantarum* (T) | 0.86 | 1.15 | 0.90 | 1.33 |
| *Corynebacterium ulcerans* (T) | 0.84 | 0.33 | 0.62 | 0.34 |
| *Propionibacterium acidipropionici* (T) | 0.84 | 0.00 | 0.00 | 0.00 |
| *Propionibacterium acidifaciens* (T) | 0.82 | 0.91 | 0.95 | 0.92 |
| *Staphylococcus succinus* (T) | 0.82 | 0.91 | 0.95 | 1.01 |
| *Propionibacterium freudenreichii* (T) | 0.82 | 1.06 | 0.93 | 0.99 |
| *Geobacillus thermodenitrificans* (T) | 0.80 | 0.63 | 0.60 | 0.53 |
| *Cupriavidus* sp. ASC-64 | 0.79 | 0.63 | 0.57 | 0.65 |
| *Geobacillus thermoleovorans* (T) | 0.78 | 0.57 | 0.02 | 0.39 |
| *Methylobacterium brachiatum* (T) | 0.77 | 0.00 | 0.00 | 0.00 |
| *Stenotrophomonas rhizophila* (T) | 0.77 | 0.98 | 0.71 | 0.82 |
| *Reyranella massiliensis* | 0.76 | 0.70 | 0.90 | 0.73 |
| *Streptococcus pyogenes* (T) | 0.74 | 0.72 | 0.11 | 0.75 |
| Cumulated Percentage Deviation from abundance estimated using full-length 16S sequences | — | 24.15 | 26.99 | 22.65 |

TABLE 8

Utility of proposed combinatorial approach in obtaining refined taxonomic profiles compared to taxonomic abundance estimates obtained with pair-wise combinations of V-regions. Results in the table pertain to the simulated Soil microbiome dataset.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Bradyrhizobium pachyrhizi* (T) | 18.72 | 16.90 | 14.83 | 14.67 |
| *Rhodomicrobium vannielii* | 5.92 | 4.24 | 7.93 | 6.47 |
| *Gemmata obscuriglobus* (T) | 5.23 | 7.60 | 7.11 | 6.93 |
| *Gemmatimonas aurantiaca* (T) | 5.16 | 7.89 | 6.41 | 6.78 |
| *Ktedonobacter racemifer* (T) | 5.03 | 7.87 | 6.94 | 7.11 |
| *Bradyrhizobium diazoefficiens* USDA 110 | 4.29 | 0.00 | 2.59 | 3.15 |
| *Bradyrhizobium japonicum* (T) | 3.97 | 0.00 | 0.00 | 0.00 |
| *Bradyrhizobium liaoningense* (T) | 3.90 | 0.00 | 0.00 | 0.00 |
| *Aguisphaera giovannonii* (T) | 3.80 | 5.34 | 4.85 | 5.62 |
| *Gaiella occulta* (T) | 2.23 | 3.19 | 2.99 | 2.52 |
| *Mycobacterium leprae* (T) | 2.17 | 3.14 | 2.42 | 2.72 |
| *Bradyrhizobium canariense* (T) | 2.16 | 3.19 | 4.89 | 3.99 |
| *Phenylobacterium muchangponense* | 2.09 | 1.54 | 1.56 | 1.72 |
| *Bradyrhizobium* sp. OO99 | 1.93 | 0.00 | 0.00 | 0.00 |
| *Bradyrhizobium rifense* | 1.61 | 0.00 | 0.00 | 0.00 |
| *Burkholderia fungorum* (T) | 1.52 | 1.16 | 1.92 | 1.82 |
| *Phenylobacterium composti* (T) | 1.45 | 2.44 | 1.88 | 2.24 |
| *Bradyrhizobium* sp. LMTR 21 | 1.44 | 1.91 | 1.75 | 1.86 |
| *Pedomicrobium ferrugineum* (T) | 1.42 | 2.11 | 1.94 | 1.79 |
| *Pedomicrobium australicum* (T) | 1.33 | 2.24 | 0.00 | 1.75 |
| *Pedomicrobium manganicum* (T) | 1.33 | 2.24 | 1.79 | 1.47 |
| *Massilia aurea* (T) | 1.29 | 1.96 | 1.88 | 1.70 |
| *Thermoleophilum album* (T) | 1.23 | 1.98 | 1.64 | 1.75 |
| *Domibacillus robiginosus* (T) | 1.15 | 1.87 | 1.88 | 1.80 |
| *Acidisoma tundrae* (T) | 1.11 | 1.67 | 1.27 | 1.70 |
| *Domibacillus* sp. NIO-1016 | 1.07 | 1.80 | 1.52 | 1.40 |
| *Acidisoma sibiricum* (T) | 0.98 | 1.45 | 1.26 | 1.15 |
| *Dyella japonica* (T) | 0.98 | 0.40 | 0.32 | 0.34 |
| *Opitutus terrae* (T) | 0.93 | 1.05 | 1.03 | 1.60 |
| *Bradyrhizobium iriomotense* (T) | 0.88 | 0.66 | 1.10 | 0.82 |
| *Tumebacillus ginsengisoli* (T) | 0.88 | 0.92 | 1.29 | 1.19 |
| *Burkholderia phenoliruptrix* (T) | 0.86 | 1.56 | 1.20 | 0.94 |
| *Burkholderia unamae* (T) | 0.85 | 0.57 | 0.68 | 0.63 |
| *Burkholderia phytofirmans* (T) | 0.84 | 0.62 | 0.67 | 0.54 |
| *Pedomicrobium americanum* (T) | 0.82 | 1.14 | 2.80 | 2.06 |
| *Burkholderia bannensis* | 0.76 | 0.02 | 0.04 | 0.02 |
| *Bradyrhizobium denitrificans* (T) | 0.73 | 0.70 | 0.91 | 0.84 |
| *Rhodopila globiformis* (T) | 0.72 | 1.19 | 0.95 | 0.97 |
| *Sinomonas atrocyanea* (T) | 0.71 | 0.22 | 0.29 | 0.24 |
| *Burkholderia tuberum* (T) | 0.66 | 0.83 | 0.67 | 0.82 |
| *Burkholderia mimosarum* (T) | 0.66 | 0.44 | 0.38 | 0.39 |
| *Microvirga* sp. BR3299 | 0.66 | 1.03 | 0.80 | 0.90 |
| *Vampirovibrio chlorellavorus* (T) | 0.61 | 0.94 | 0.95 | 0.82 |
| *Burkholderia sediminicola* (T) | 0.61 | 0.00 | 0.38 | 0.26 |
| *Legionella pneumophila* (T) | 0.58 | 0.83 | 0.87 | 0.79 |
| *Burkholderia udeis* | 0.57 | 0.09 | 0.06 | 0.10 |
| *Chromobacterium vaccinii* (T) | 0.54 | 0.73 | 0.82 | 0.66 |
| *Segetibacter koreensis* (T) | 0.54 | 0.70 | 0.70 | 0.98 |
| *Phenylobacterium falsum* (T) | 0.53 | 0.79 | 0.76 | 0.74 |
| *Phenylobacterium immobile* (T) | 0.53 | 0.83 | 1.08 | 1.23 |
| Cumulated Percentage Deviation from abundance estimated using full-length 16S sequences | — | 47.96 | 44.05 | 40.99 |

TABLE 9

Utility of proposed combinatorial approach in obtaining refined taxonomic profiles compared to taxonomic abundance estimates obtained with pair-wise combinations of V-regions. Results in the table pertain to the simulated Aquatic microbiome dataset.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Polynucleobacter necessarius* (T) | 31.17 | 36.21 | 36.30 | 36.01 |
| *Polynucleobacter cosmopolitanus* (T) | 12.68 | 14.48 | 13.55 | 13.85 |
| *Mycobacterium leprae* | 5.91 | 6.74 | 6.67 | 6.84 |
| *Luteolibacter algae* (T) | 3.90 | 4.73 | 4.64 | 4.50 |
| *Rhodoferax saidenbachensis* ED16 | 3.13 | 2.00 | 0.82 | 1.78 |
| *Polynucleobacter acidiphobus* (T) | 2.60 | 3.04 | 2.95 | 2.83 |
| *Acidovorax delafieldii* (T) | 2.35 | 0.58 | 0.37 | 0.46 |
| *Rhodoferax antarcticus* (T) | 2.09 | 2.36 | 2.26 | 2.29 |
| *Acidovorax temperans* (T) | 1.85 | 0.58 | 0.66 | 0.54 |
| *Methylophilus methylotrophus* (T) | 1.69 | 0.86 | 0.59 | 0.80 |
| *Rhodoferax fermentans* (T) | 1.69 | 1.87 | 1.85 | 2.17 |
| *Opitutus terrae* (T) | 1.60 | 1.85 | 1.91 | 2.03 |
| *Luteolibacter pohnpeiensis* (T) | 1.56 | 1.87 | 1.85 | 1.86 |
| *Haliscomenobacter hydrossis* (T) | 1.35 | 1.59 | 1.63 | 1.54 |
| *Acidovorax cattleyae* (T) | 1.27 | 1.50 | 2.51 | 1.82 |
| *Mycobacterium iranicum* (T) | 1.26 | 1.48 | 1.44 | 1.45 |
| *Mycobacterium novocastrense* (T) | 1.16 | 1.27 | 1.40 | 1.35 |
| *Mycobacterium marinum* (T) | 1.13 | 0.00 | 0.00 | 0.00 |
| *Methylomonas methanica* (T) | 1.03 | 0.06 | 0.04 | 0.09 |
| *Mycobacterium tuberculosis* (T) | 1.01 | 0.00 | 0.00 | 0.00 |
| *Microbacterium paraoxydans* (T) | 0.99 | 1.04 | 1.10 | 0.83 |
| *Algoriphagus namhaensis* | 0.97 | 1.13 | 1.00 | 1.10 |
| *Polynucleobacter rarus* (T) | 0.96 | 1.08 | 1.09 | 0.95 |
| *Mycobacterium cookii* (T) | 0.95 | 1.20 | 1.07 | 1.11 |
| *Acidovorax caeni* (T) | 0.93 | 1.13 | 1.03 | 1.08 |
| *Mycobacterium arupense* (T) | 0.93 | 0.00 | 0.00 | 0.00 |
| *Flavobacterium degerlachei* (T) | 0.80 | 0.33 | 0.72 | 0.59 |
| *Methylomonas koyamae* (T) | 0.78 | 0.59 | 0.94 | 0.95 |
| *Acidovorax avenae* (T) | 0.72 | 0.00 | 0.00 | 0.00 |
| *Methylophilus leisingeri* (T) | 0.71 | 0.82 | 1.41 | 0.95 |
| *Rhodomicrobium vannielii* | 0.71 | 0.39 | 0.88 | 0.71 |
| *Fluviicola taffensis* | 0.70 | 0.87 | 0.84 | 0.89 |
| *Comamonas testosteroni* (T) | 0.67 | 0.65 | 0.68 | 0.76 |
| *Beijerinckia indica* (T) | 0.64 | 0.77 | 0.76 | 0.81 |
| *Algoriphagus antarcticus* (T) | 0.62 | 0.73 | 0.69 | 0.72 |
| *Acidovorax radicis* (T) | 0.61 | 0.00 | 0.00 | 0.00 |
| *Methylocystis rosea* (T) | 0.57 | 0.58 | 1.07 | 0.75 |
| *Methylomonas scandinavica* (T) | 0.57 | 0.34 | 0.66 | 0.47 |
| *Methylophilus flavus* (T) | 0.57 | 0.36 | 0.35 | 0.37 |
| *Stenotrophomonas rhizophila* (T) | 0.55 | 0.61 | 0.50 | 0.53 |
| *Methylocystis hirsuta* (T) | 0.53 | 0.47 | 0.00 | 0.27 |
| *Comamonas jiangduensis* (T) | 0.51 | 0.06 | 0.06 | 0.09 |
| *Algoriphagus halophilus* (T) | 0.50 | 0.61 | 0.60 | 0.61 |
| *Algoriphagus lutimaris* (T) | 0.49 | 0.52 | 0.60 | 0.45 |
| *Verrucomicrobium spinosum* (T) | 0.45 | 0.52 | 0.54 | 0.60 |
| *Acidovorax konjaci* (T) | 0.44 | 0.13 | 0.10 | 0.18 |
| *Aguisphaera giovannonii* (T) | 0.44 | 0.55 | 0.56 | 0.60 |
| *Belnapia moabensis* (T) | 0.44 | 0.52 | 0.50 | 0.54 |
| *Caulobacter henricii* (T) | 0.40 | 0.47 | 0.34 | 0.43 |
| *Prosthecobacter vanneervenii* (T) | 0.40 | 0.49 | 0.44 | 0.44 |
| Cumulated Percentage Deviation from abundance estimated using full-length 16S sequences | — | 25.26 | 27.39 | 24.93 |

TABLE 10

Utility of proposed combinatorial approach in obtaining refined taxonomic profiles compared to taxonomic abundance estimates obtained with pair-wise combinations of V-regions. Results in the table pertain to the simulated human gut microbiome dataset Vagina. While the chosen pairs of V-regions appear to provide sub-optimal performance for the Vaginal microbiome dataset, using a different set of V-region pairs (e.g. V1 + V5 and V1 + V8) improves the results of the combinatorial approach.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Lactobacillus plantarum* (T) | 24.11 | 26.50 | 24.97 | 24.72 |
| *Lactobacillus paracasei* (T) | 14.14 | 15.43 | 14.90 | 14.73 |
| *Lactobacillus fermentum* | 8.94 | 9.45 | 9.22 | 9.75 |
| *Lactobacillus delbrueckii* (T) | 7.71 | 8.43 | 7.83 | 7.95 |
| *Prevotella amnii* (T) | 4.99 | 0.00 | 5.34 | 5.30 |
| *Prevotella nigrescens* (T) | 4.82 | 5.37 | 5.12 | 5.18 |
| *Sneathia sanguinegens* (T) | 4.39 | 4.80 | 4.61 | 4.43 |
| *Atopobium rimae* (T) | 2.70 | 1.06 | 0.93 | 0.96 |
| *Lactobacillus reuteri* (T) | 2.26 | 2.54 | 2.39 | 2.33 |
| *Lactobacillus diolivorans* (T) | 2.10 | 2.29 | 2.45 | 2.34 |
| *Lactobacillus farraginis* (T) | 1.60 | 1.63 | 1.38 | 1.38 |
| *Lactobacillus sakei* (T) | 1.59 | 1.81 | 1.54 | 1.51 |
| *Lactobacillus amylovorus* (T) | 1.22 | 1.40 | 1.29 | 1.43 |
| *Lactobacillus kimchii* (T) | 1.13 | 0.37 | 0.42 | 0.29 |
| *Lactobacillus gasseri* (T) | 1.04 | 1.18 | 0.99 | 1.03 |
| *Atopobium minutum* (T) | 0.98 | 1.08 | 1.04 | 1.11 |
| *Lactobacillus kefiri* (T) | 0.97 | 1.17 | 0.97 | 0.94 |
| *Lactobacillus futsaii* | 0.91 | 0.89 | 0.91 | 0.84 |
| *Lactobacillus kefiranofaciens* (T) | 0.86 | 0.99 | 0.89 | 0.80 |
| *Lactobacillus farciminis* | 0.79 | 0.18 | 0.18 | 0.18 |
| *Finegoldia magna* (T) | 0.76 | 0.80 | 0.85 | 0.75 |
| *Lactobacillus buchneri* (T) | 0.73 | 0.90 | 0.78 | 0.80 |
| *Parvimonas micra* (T) | 0.73 | 0.90 | 0.87 | 0.75 |
| *Lactobacillus mucosae* (T) | 0.64 | 0.68 | 0.73 | 0.69 |
| *Lactobacillus animalis* (T) | 0.61 | 0.68 | 0.57 | 0.76 |
| *Lactobacillus parabuchneri* (T) | 0.58 | 0.71 | 0.59 | 0.46 |
| *Lactobacillus florum* (T) | 0.56 | 0.66 | 0.72 | 0.61 |
| *Lactobacillus kunkeei* (T) | 0.55 | 0.62 | 0.55 | 0.61 |
| *Dialister invisus* (T) | 0.55 | 0.55 | 0.58 | 0.68 |
| *Streptococcus salivarius* (T) | 0.55 | 0.50 | 0.57 | 0.40 |
| *Lactobacillus coryniformis* (T) | 0.49 | 0.59 | 0.46 | 0.53 |
| *Aerococcus viridans* | 0.45 | 0.23 | 0.07 | 0.13 |
| *Lactobacillus vaccinostercus* (T) | 0.45 | 0.55 | 0.51 | 0.48 |
| *Lactobacillus ingluviei* (T) | 0.41 | 0.42 | 0.28 | 0.34 |
| *Anaerococcus murdochii* (T) | 0.40 | 0.54 | 0.30 | 0.26 |
| *Lactobacillus helveticus* (T) | 0.36 | 0.00 | 0.33 | 0.31 |
| *Anaerococcus vaginalis* (T) | 0.36 | 0.44 | 0.35 | 0.41 |
| *Streptococcus suis* (T) | 0.36 | 0.32 | 0.40 | 0.33 |
| *Lactobacillus paracollinoides* (T) | 0.33 | 0.30 | 0.29 | 0.35 |
| *Dialister pneumosintes* (T) | 0.32 | 0.35 | 0.35 | 0.33 |
| *Lactobacillus vaginalis* (T) | 0.30 | 0.31 | 0.22 | 0.46 |
| *Lactobacillus oeni* (T) | 0.28 | 0.37 | 0.27 | 0.30 |
| *Mobiluncus curtisii* (T) | 0.27 | 0.30 | 0.25 | 0.36 |
| *Lactobacillus crustorum* (T) | 0.25 | 0.21 | 0.23 | 0.23 |
| *Lactobacillus rossiae* (T) | 0.25 | 0.15 | 0.36 | 0.15 |
| *Ureaplasma urealyticum* (T) | 0.25 | 0.30 | 0.28 | 0.30 |
| *Lactobacillus harbinensis* (T) | 0.24 | 0.23 | 0.17 | 0.18 |
| *Lactobacillus acetotolerans* (T) | 0.24 | 0.22 | 0.22 | 0.28 |
| *Streptococcus agalactiae* (T) | 0.24 | 0.28 | 0.28 | 0.29 |
| *Lactobacillus sunkii* (T) | 0.23 | 0.30 | 0.21 | 0.25 |
| Cumulated Percentage Deviation from abundance estimated using full-length 16S sequences | — | 17.80 | 8.83 | 9.50 |

TABLE 11

Utility of proposed combinatorial approach in obtaining refined taxonomic profiles compared to taxonomic abundance estimates obtained with pair-wise combinations of V-regions. Results in the table pertain to the simulated Nematode-gut microbiome dataset.

| Species | Abundance (%) estimated with full-length 16S reads | Abundance (%) estimated with 10000 V1 + V4 paired-end reads | Abundance (%) estimated with 10000 V1 + V5 paired-end reads | Abundance (%) estimated with combinatorial approach using 5000 V1 + V4 and 5000 V1 + V5 reads |
|---|---|---|---|---|
| *Acinetobacter baumannii* (T) | 8.40 | 10.44 | 8.59 | 9.11 |
| *Cellvibrio vulgaris* (T) | 7.93 | 0.00 | 10.13 | 9.66 |
| *Cellvibrio japonicus* (T) | 6.24 | 8.52 | 7.97 | 7.38 |
| *Cellvibrio fibrivorans* (T) | 4.60 | 2.02 | 6.16 | 3.87 |
| *Reyranella massiliensis* | 3.58 | 5.31 | 5.24 | 4.08 |
| *Pseudoalteromonas tetraodonis* (T) | 3.58 | 4.76 | 4.62 | 3.65 |
| *Enhydrobacter aerosaccus* (T) | 3.57 | 4.91 | 4.39 | 4.58 |
| *Acinetobacter calcoaceticus* (T) | 3.47 | 4.21 | 2.82 | 3.22 |
| *Cellvibrio mixtus* (T) | 3.17 | 4.01 | 4.07 | 3.37 |
| *Cellvibrio* sp. E50 | 3.06 | 4.04 | 0.00 | 3.43 |
| *Marinomonas primoryensis* (T) | 2.62 | 0.00 | 0.00 | 0.00 |
| *Acinetobacter lwoffii* (T) | 2.42 | 2.67 | 2.34 | 2.18 |
| *Escherichia/Shigella flexneri* (T) | 2.15 | 0.00 | 0.00 | 0.00 |
| *Escherichia/Shigella fergusonii* (T) | 2.15 | 2.89 | 0.00 | 2.37 |
| *Escherichia/Shigella dysenteriae* (T) | 2.12 | 2.54 | 2.76 | 2.57 |
| *Staphylococcus aureus* (T) | 2.09 | 2.82 | 2.62 | 2.43 |
| *Escherichia/Shigella albertii* (T) | 2.01 | 2.72 | 2.87 | 2.30 |
| *Alkanindiges illinoisensis* (T) | 1.94 | 2.49 | 2.62 | 2.37 |
| *Pseudomonas aeruginosa* (T) | 1.76 | 2.47 | 2.30 | 2.02 |
| *Arcobacter butzleri* (T) | 1.74 | 2.14 | 2.16 | 1.66 |
| *Cellvibrio fulvus* (T) | 1.74 | 2.27 | 2.32 | 2.04 |
| *Propionibacterium acnes* (T) | 1.70 | 2.29 | 2.30 | 2.02 |
| *Cellvibrio gandavensis* (T) | 1.63 | 2.27 | 1.75 | 1.92 |
| *Cellvibrio ostraviensis* (T) | 1.60 | 2.19 | 2.04 | 2.04 |
| *Marinomonas arctica* (T) | 1.56 | 1.94 | 1.79 | 1.94 |
| *Oceanospirillum maris* (T) | 1.45 | 2.24 | 2.00 | 1.83 |
| *Peredibacter starrii* (T) | 1.39 | 1.84 | 1.79 | 1.54 |
| *Pseudoalteromonas arctica* (T) | 1.31 | 0.00 | 0.00 | 0.00 |
| *Delftia lacustris* (T) | 1.25 | 0.00 | 0.00 | 0.00 |
| *Oleispira antarctica* (T) | 1.17 | 1.54 | 1.54 | 1.52 |
| *Oceanospirillum beijerinckii* (T) | 1.08 | 1.50 | 1.47 | 1.44 |
| *Acinetobacter junii* (T) | 1.06 | 1.57 | 1.15 | 1.10 |
| *Listonella anguillarum* (T) | 1.01 | 0.22 | 0.78 | 0.54 |
| *Brevundimonas naejangsanensis* (T) | 1.01 | 1.00 | 1.19 | 1.33 |
| *Pseudoalteromonas shioyasakiensis* | 0.96 | 0.95 | 1.19 | 0.93 |
| *Oceanospirillum linum* | 0.89 | 0.72 | 1.10 | 1.22 |
| *Vibrio cholerae* (T) | 0.87 | 0.00 | 0.02 | 0.08 |
| *Brevundimonas diminuta* (T) | 0.82 | 1.10 | 0.02 | 0.97 |
| *Persicirhabdus sediminis* (T) | 0.82 | 1.37 | 1.06 | 0.97 |
| *Leucobacter chromiiresistens* (T) | 0.82 | 0.00 | 0.00 | 0.00 |
| *Acinetobacter radioresistens* (T) | 0.80 | 1.20 | 0.90 | 0.97 |
| *Brevundimonas terrae* (T) | 0.77 | 0.35 | 0.34 | 0.35 |
| *Vibrio rotiferianus* (T) | 0.77 | 0.55 | 0.02 | 0.59 |
| *Acinetobacter guillouiae* (T) | 0.76 | 0.37 | 0.83 | 0.66 |
| *Leucobacter tardus* (T) | 0.76 | 1.02 | 0.85 | 0.95 |
| *Brevundimonas bullata* (T) | 0.72 | 1.00 | 0.23 | 0.76 |
| *Leucobacter komagatae* (T) | 0.71 | 0.17 | 0.23 | 0.23 |
| *Microbacteriaceae bacterium* DSM 27064 | 0.67 | 0.52 | 0.21 | 0.56 |
| *Acinetobacter nectaris* (T) | 0.66 | 0.85 | 0.62 | 0.67 |
| *Brevundimonas intermedia* (T) | 0.64 | 0.00 | 0.62 | 0.59 |
| Cumulated Percentage Deviation from abundance estimated using full-length 16S sequences | — | 45.74 | 37.26 | 24.19 |

Method for Generation of the Computation Table

Rationale and methodology employed for pre-computing/pre-estimating the accuracies of (a) the individual V-regions (targeted in the experiments) in resolving each of the taxonomic groups under consideration.

(b) Pairs of (contiguously or non-contiguously located) V-regions within the 16S rRNA gene in resolving each of the taxonomic groups under consideration.

As a one-time procedure, the following steps were performed for pre-computing the discriminating capability i.e. the accuracy of different V-regions (or combinations of various possible pairs of the same) with respect to different taxonomic lineages. The pre-generated set of accuracy values are required for solving Equation 3.

Rationale and Procedure

Full length bacterial 16S rRNA gene sequences (along with their annotated lineages) present in the RDP database (release 11.3) were retrieved. The RDP hierarchy browser was used for this purpose with the following filters—Strain='Both'; Source='Isolates'; Size '>=1200'; Taxonomy='NCBI'; Quality='Good', which resulted in a downloaded set of 232,163 sequences. Further, sequences not containing any of the nine V-regions (V1-V9) were filtered out from the set of sequences, leaving a total of 84,711 16S rRNA sequences belonging to 11,810 species. Subsequently, both full-length as well as different portions of the 16S rRNA gene sequences were extracted in silico to represent outcomes of amplicon sequencing experiments, and were provided as input to the Wang classifier (algorithm used in RDP classifier), for taxonomic classification. The current version of RDP classifier 16S training set was used as the reference database for these taxonomic assignment steps, and the taxonomic hierarchy information of the reference sequences were appropriately used while training the Wang classifier in order to enable obtaining taxonomic classifications resolved up to species level. Only a subset (57,632 sequences) of the originally downloaded full-length 16S rRNA gene sequences, which could be classified at species level with >=80% bootstrap confidence threshold, was later used as a pool for randomly drawing sequences during creation of mock/simulated metagenomic datasets (as described later in this section).

For evaluating the discriminating ability of individual V-regions and their combinations, the regions of interest were parsed out from corresponding full-length 16S rRNA gene sequences using an in house modified version of the V-xtractor program, and submitted as query sequences to the Wang classifier, after appropriate pre-processing. First, the effectiveness of individual V-regions in resolving between different taxonomic groups was evaluated. For this purpose, different V-regions from all the 16S rRNA gene sequences, downloaded from the RDP database, were extracted. Subsequently, each of these individual V-regions were subjected to taxonomic classification with the Wang classifier, and the resultant assignments at the genus level were checked for accuracy and specificity against the taxonomic attributes provided by RDP for the corresponding full-length sequences.

Figure 6:
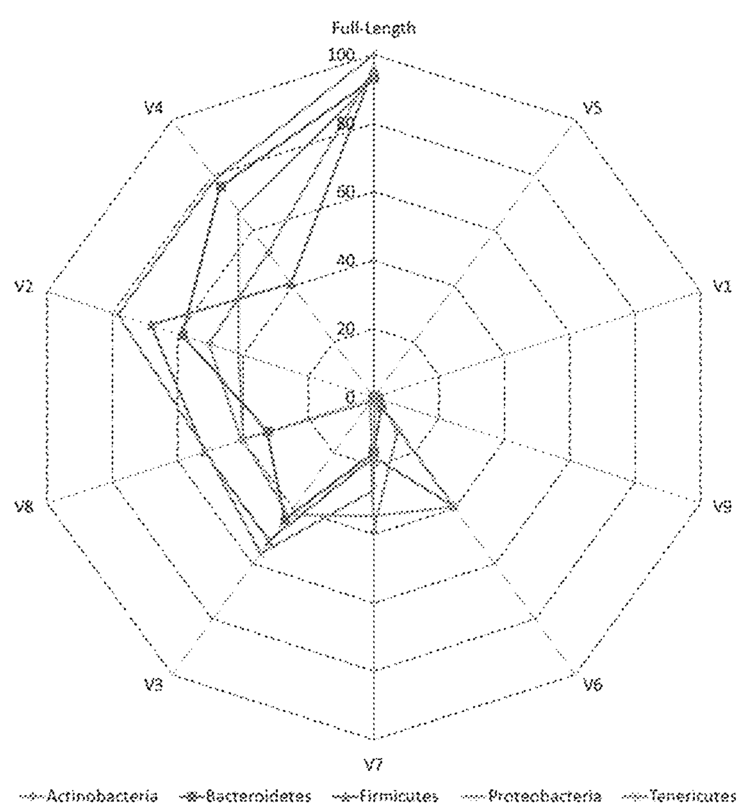
FIG. 6 shows a plot depicting the percentage of 16S rRNA genes present in RDP database that could be correctly classified utilizing different variable (V) regions according to an embodiment of the disclosure.

The taxonomic classification accuracies of different V-regions in resolving different taxonomic groups are depicted in FIG. 6. The taxonomic classification accuracies (at genus level) obtained with V-regions have been cumulated and depicted at the 'phylum level' in the figure, and placed in context with the taxonomic classification accuracies which would have been obtained with full length 16S rRNA gene sequences.

Except for V1, V5 and V9, all other V-regions were observed to have certain utility in taxonomic classification, even when targeted individually. It was also evident from the plot that some V-regions provide comparatively higher taxonomic classification accuracies of classification for specific taxonomic groups. For example, the V4 region has the highest accuracy while classifying sequences pertaining to the phylum Bacteroidetes (75.9%), whereas the V2 region classifies best with respect to the phylum Firmicutes (68.2%). A detailed list of taxonomic classification accuracies in taxonomic classification obtained with different V-regions at genus level is also calculated and collated in a table (not provided in the disclosure due to large size).

Given these observations, it would seem logical for a microbiome study design to sequence two (or more) V-regions from a 16S rRNA gene fragment which have complementary abilities with respect to classification of different taxonomic groups. Furthermore, the choice of the combination of V-regions could also be guided by the environment from where the metagenomic sample is being collected, given that diverse environments may be differentially enriched with different taxonomic groups. A preferred combination of V-regions cannot always be expected to be situated in a contiguous stretch on the 16S rRNA gene. Given the read length limitations of NGS technologies, targeting an amplicon constituting the preferred regions becomes difficult in reality.

Figure 7:
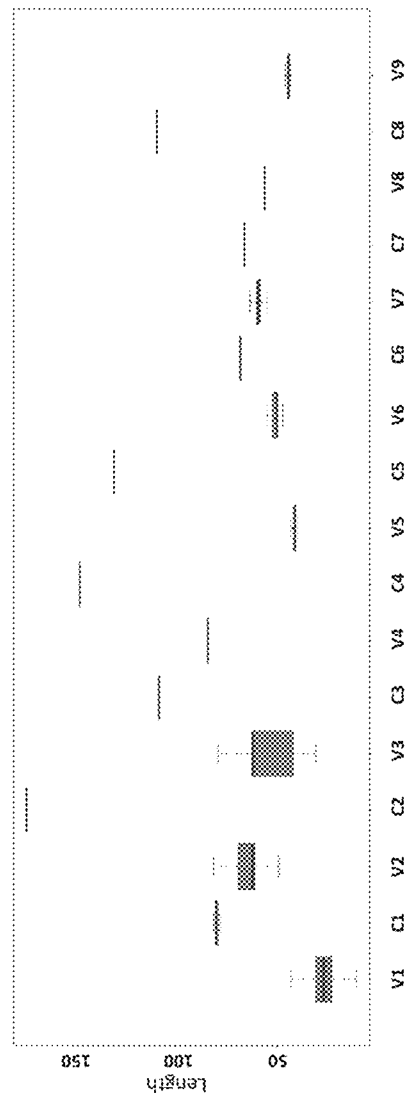
FIG. 7 shows length distributions (in bp) of different variable (V) and constant (C) regions across 84711 different bacterial 16s rRNA genes retrieved from the RDP database according to an embodiment of the disclosure.

The length distributions of V-regions and C-regions (constant/conserved regions flanking the V-regions) across different bacterial taxonomic groups are provided in FIG. 7. These distributions indicate that while individual V-regions and contiguous stretches like V2-V3 (median length 297 bp) or V3-V4 (median length 254 bp) can easily be targeted with short read sequencing techniques like Illumina HiSeq/MiSeq, sequencing longer contiguous stretches encompassing more than two V-regions, such as V2-V3-V4 (median length 482 bp) and V4-V5-V6 (median length 453 bp) necessitates sequencing platforms that can generate longer read lengths.

Figure 8:
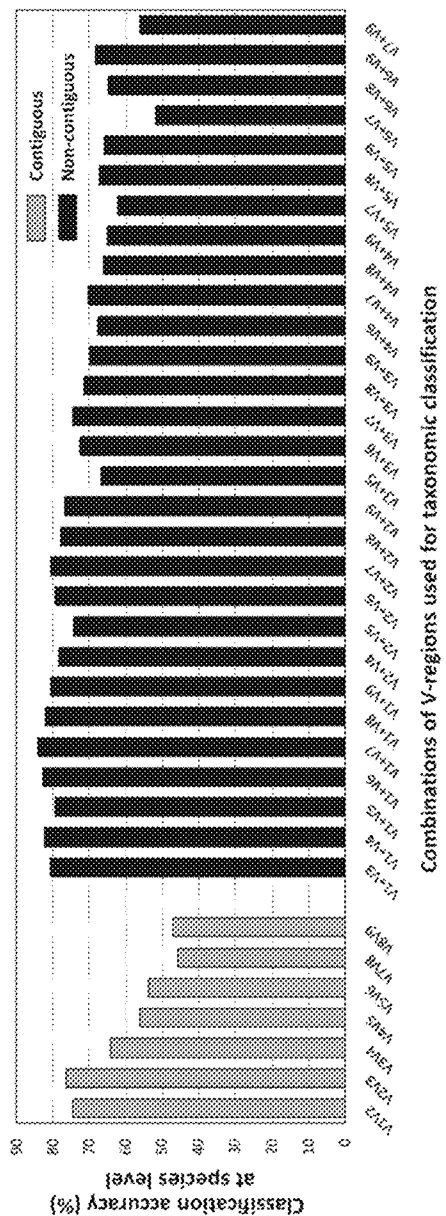
FIG. 8 shows taxonomic classification accuracies obtained using different pair wise combinations of V-regions (both contiguous as well as non-contiguous). Combinations of V-regions achieving a classification accuracy of >=70% are also shown according to an embodiment of the disclosure.

Paired-end sequencing protocols available with some of the NGS platforms allow sequencing of a stretch of DNA from both its ends. For example, Illumina HiSeq sequencing platforms can be used for paired-end sequencing to generate up to 2×250 bp reads. The current work proposes, and evaluates in silico, the utilization of paired-end sequencing protocols for sequencing various pair wise combinations of non-contiguous V-regions in a single sequencing run. To this end, appropriate primers need to be designed against a desired stretch of the 16S rRNA gene, such that the targeted V-regions (either contiguously or non-contiguously placed) reside within this stretch, and are not far from either of its boundaries. Sequencing of the amplicons generated with these primers can then be performed with a paired-end sequencing protocol, whereby these (amplified) stretches of DNA are sequenced from both ends. Two reads sequenced from each such amplicon would cover the two targeted V-regions (one from each end). Since each of the sequenced reads from any given 'pair' targets a single V-region (situated at one of the ends of the amplicon), read-length limitations do not restrict capturing the entirety of the individual V-regions. Consequently, it becomes possible to sequence almost all possible pair wise combinations of V-regions, either arranged contiguously or non-contiguously. The results pertaining to the in silico evaluation of the effectiveness of different combinations of V-regions (see Methods), in providing accurate taxonomic classifications (at the species level) for sequences listed in the RDP database, is depicted in FIG. 8.

Figure 9:
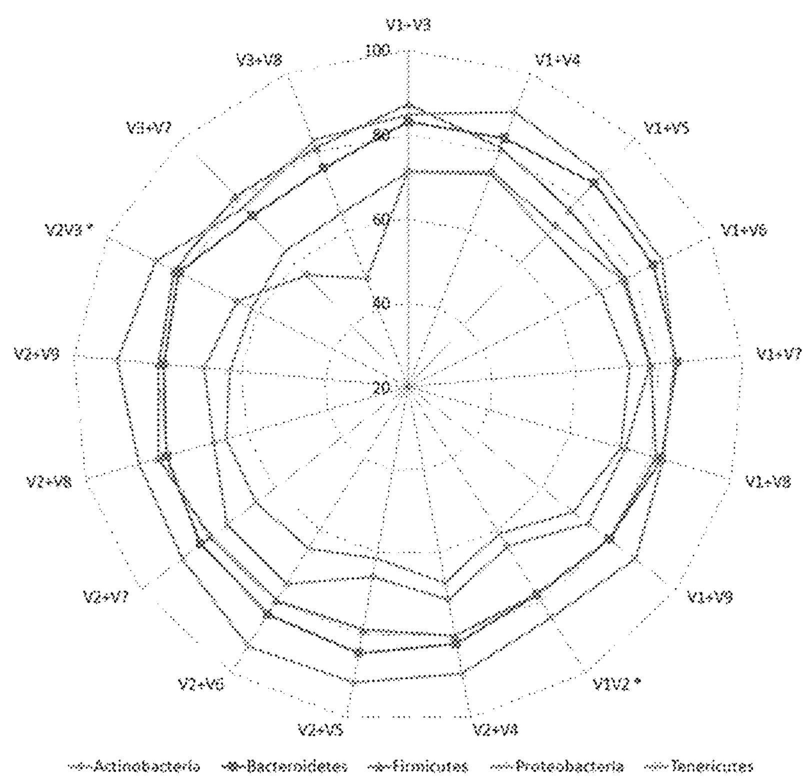
FIG. 9 shows a plot depicting the taxonomic classification accuracies obtained at species level using different pair wise combinations of V-regions (both contiguous as well as non-contiguous) drawn from the 16S rRNA genes according to an embodiment of the disclosure.

Taxonomic classification accuracies provided by several combinations of non-contiguously placed V-region pairs, namely V1+V3 (77.7%), V1+V4 (77.4%), V1+V8 (76.6%), V2+V5 (73.6%), etc., were sufficiently high, and exceeded the taxonomic classification accuracies provided by combination of adjacently placed V-regions by a fair margin. It was also significant to note that many of the individual V-regions, which had very low taxonomic discriminating ability of their own (FIG. 6), could provide significant taxonomic classification accuracies when paired up with other V-regions. For example, while V1 and V5 provided very low taxonomic classification accuracies when targeted alone, the combination of V1+V5 could provide a significantly high taxonomic classification accuracy of 73.4%. Furthermore, although the individual V-regions were observed to have differential abilities in classifying sequences originating from different phyla (FIG. 6), their combinations were much more coherent in this regard, and could classify sequences from all phyla with almost equivalent efficiency (FIG. 9). Results indicate the potential utility of targeting pairs of non-contiguously placed V-regions to improve taxonomic classification accuracy. Additionally, the results also suggest that for exploring the taxonomic diversity of a particular environment, which may be expected to be enriched with particular groups of bacteria, an appropriate combination of V-regions sensitive to the same bacterial groups may be chosen.

It may be noted in this context, that reads generated during amplicon sequencing may often encompass flanking 'constant' regions in addition to the targeted V-region(s), depending on choice of primers and the maximum read-length attainable by the sequencing technology. Consequently, our evaluation exercise, pertaining to combination of V-regions, aimed at mimicking 250 bp×2 paired-end sequencing, wherein the extracted regions (representing sequenced reads) also encompass such flanking regions. To achieve this, regions from the full length 16S rRNA genes were extracted in such a way that either of the 250 bp reads (constituting a read-pair) contained one of the target V-regions, flanked in both directions by equivalent portions (lengths) of the surrounding 'constant' regions. HMMs corresponding to constant regions surrounding the V-regions, as provided by the V-xtractor program were used for this purpose. In case two adjacent V-regions were targeted, there was a significant chance of finding an overlap between two reads constituting a pair. This overlap was utilized to join the pair of reads together into a single sequence before submitting the same as a query to the Wang classifier. In contrast, on sequencing two distantly separated non-contiguous V-regions, no overlap between the read pairs could be expected. Accordingly, the pair of reads in this case were concatenated using a string of eight consecutive 'N's, while preserving their orientation, prior to processing with Wang classifier. Given that Wang classifier (or RDP classifier) utilizes 8-mer nucleotide frequencies during taxonomic assignment, joining two non-overlapping sequenced fragments with 8 ambiguous nucleotides (N) ensures avoiding generation of spurious 8-mers consisting nucleotides from non-adjacent regions of the gene. Taxonomic assignments generated by the Wang classifier at a predetermined taxonomic level with a confidence threshold score of >=80% were used for all downstream comparative analyses.

The utility of all possible pair wise combinations of V regions, either arranged contiguously or non-contiguously, were investigated in silico in terms of accuracy of taxonomic classifications provided by each such combination. As mentioned earlier, sequence fragments mimicking outcomes of 250 bp×2 paired-end sequencing, which target different contiguous/non-contiguous combinations of V-regions, were derived from the downloaded 16S rRNA gene sequences. These fragments were subsequently subjected to taxonomic classification with the Wang classifier and the assignments obtained at species level were checked for accuracy and specificity against the pre-annotated taxonomic attributes of their source (full-length) 16S rRNA genes.

To assess the utility of the proposed non-contiguous combination of V-regions on a microbiome dataset, while avoiding any bias arising out of the proportion of sequences pertaining to different bacterial groups currently catalogued in reference databases like RDP, taxonomic classification exercises were further performed with mock and simulated metagenomic datasets.

Each of the mock microbiome datasets were constructed using 10,000 randomly selected 16S rRNA gene sequences from one of the five randomized 16S gene pools. Each of these gene pools consisted of sequences downloaded from the RDP database, wherein the proportion of sequences selected from different organisms were also randomized (see Methods). The results, in terms of classification accuracy at the species level, are depicted in Table 12. It was interesting to note that 18 out of the 20 combinations of V-regions, which could provide classification accuracy >=60% on average, constituted of non-contiguous V-regions. The best performing combination of adjacent V-regions was V2-V3, which on average provided 69.1% classification accuracy. In comparison, the combination of the non-contiguously placed V-regions V1+V4 demonstrated a high average classification accuracy of 77.2%.

TABLE 12

Taxonomic classification accuracies obtained using different pair-wise combinations of V-regions (both contiguous as well as non-contiguous) evaluated for mock microbiome datasets, each constituting of 10,000 randomly selected 16S rRNA genes from five different 16S gene pools. Accuracy of taxonomic assignments has been evaluated at the species level considering the assignments obtained with full-length 16S sequences to be correct. Top 20 combinations in terms of average classification accuracy have been depicted.

| | Classification accuracy (%) at species level averaged over five mock datasets from each 16S gene pool | | | | | |
|---|---|---|---|---|---|---|
| Combination of V-region | Mock data from 16S gene pool 1 | Mock data from 16S gene pool 2 | Mock data from 16S gene pool 3 | Mock data from 16S gene pool 4 | Mock data from 16S gene pool 5 | Average accuracy |
| V1 + V4 | 77.29 | 79.47 | 72.79 | 75.9 | 80.48 | 77.19 |
| V1 + V3 | 74.69 | 78.16 | 77.52 | 74.76 | 80.08 | 77.04 |
| V1 + V8 | 76.03 | 77.96 | 73.24 | 75.72 | 79.32 | 76.46 |
| V1 + V7 | 77.2 | 78.33 | 70.37 | 77.34 | 78.6 | 76.37 |
| V1 + V6 | 72.46 | 77.34 | 69.73 | 78.25 | 76.9 | 74.94 |
| V1 + V5 | 70.89 | 74.24 | 69.16 | 73.37 | 76.4 | 72.81 |
| V1 + V9 | 71.74 | 71.41 | 71.33 | 73.95 | 75.57 | 72.8 |
| V2 + V4 | 69.07 | 75.07 | 72.76 | 70.99 | 73.55 | 72.29 |
| V2 + V8 | 68.26 | 74.6 | 73.33 | 70.66 | 73.27 | 72.02 |
| V2 + V6 | 66.84 | 74.54 | 72.6 | 72.19 | 72.67 | 71.77 |
| V2 + V7 | 68.34 | 72.76 | 72.73 | 71.17 | 71.3 | 71.26 |
| V2V3* | 61.53 | 71.52 | 72.03 | 66.31 | 73.92 | 69.06 |
| V2 + V9 | 65.03 | 68.85 | 71.6 | 66.32 | 71.81 | 68.72 |
| V1V2* | 64.2 | 70.29 | 66.81 | 65.44 | 72.4 | 67.83 |
| V3 + V8 | 68.47 | 61.8 | 69.66 | 66.59 | 67.82 | 66.87 |
| V3 + V7 | 68.41 | 61.6 | 71.05 | 66.8 | 65.93 | 66.76 |

TABLE 12-continued

Taxonomic classification accuracies obtained using different pair-wise combinations of V-regions (both contiguous as well as non-contiguous) evaluated for mock microbiome datasets, each constituting of 10,000 randomly selected 16S rRNA genes from five different 16S gene pools. Accuracy of taxonomic assignments has been evaluated at the species level considering the assignments obtained with full-length 16S sequences to be correct. Top 20 combinations in terms of average classification accuracy have been depicted.

| | Classification accuracy (%) at species level averaged over five mock datasets from each 16S gene pool | | | | | |
|---|---|---|---|---|---|---|
| Combination of V-region | Mock data from 16S gene pool 1 | Mock data from 16S gene pool 2 | Mock data from 16S gene pool 3 | Mock data from 16S gene pool 4 | Mock data from 16S gene pool 5 | Average accuracy |
| V2 + V5 | 61.38 | 68.19 | 68.42 | 65.36 | 69.34 | 66.54 |
| V3 + V6 | 63.26 | 59.91 | 68.53 | 67.04 | 65.15 | 64.78 |
| V3 + V9 | 63.63 | 55.85 | 67.2 | 65.94 | 63.83 | 63.29 |
| V3 + V5 | 60.94 | 56.74 | 65.79 | 62.91 | 62.49 | 61.77 |

The specific combinations of V-regions, which provided comparatively higher accuracies of taxonomic classification with the RDP database sequences, were made subject to this further evaluation wherein 5 mock 16S metagenomic gene pools were created from randomly selected sets of 50 organisms (genus) listed in RDP database (Table 13).

TABLE 13

Source genera for 16S rRNA sequences included in five 16S gene pools. Randomly drawn sequences from these pools were used in generation of mock datasets.

| Genera pool 1 | 16S gene pool 2 | 16S gene pool 3 | 16S gene pool 4 | 16S gene pool 5 | 16S gene |
|---|---|---|---|---|---|
| Acetobacterium | No | No | No | Yes | No |
| Achromobacter | Yes | No | Yes | No | No |
| Acidiphilium | No | No | No | No | Yes |
| Acidithiobacillus | No | Yes | No | No | No |
| Acidovorax | Yes | No | No | No | No |
| Acinetobacter | Yes | No | No | Yes | No |
| Actinobacillus | Yes | No | No | No | No |
| Actinomadura | No | No | Yes | No | Yes |
| Aggregatibacter | No | Yes | No | Yes | Yes |
| Agromyces | No | No | No | No | Yes |
| Alcaligenes | Yes | No | No | No | No |
| Alcanivorax | No | Yes | No | No | No |
| Alicyclobacillus | No | No | No | No | Yes |
| Alkalibacterium | No | No | No | No | Yes |
| Alteromonas | No | No | No | No | Yes |
| Arcobacter | Yes | No | No | No | Yes |
| Arthrobacter | Yes | Yes | Yes | Yes | No |
| Asaia | No | No | Yes | No | No |
| Azoarcus | Yes | No | No | No | No |
| Azospirillum | No | Yes | Yes | No | No |
| Bacillus | No | No | Yes | No | No |
| Bifidobacterium | No | Yes | No | No | Yes |
| Borrelia | No | No | No | Yes | Yes |
| Bosea | No | No | Yes | Yes | No |
| Brachybacterium | No | No | Yes | No | No |
| Bradyrhizobium | No | Yes | Yes | Yes | No |
| Brevibacillus | Yes | No | No | No | No |
| Brevundimonas | Yes | No | No | No | No |
| Brucella | Yes | No | No | No | No |
| Buchnera | Yes | No | Yes | No | Yes |
| Burkholderia | No | No | No | Yes | No |
| Butyrivibrio | Yes | No | Yes | Yes | No |
| Campylobacter | Yes | No | No | No | No |
| Carnobacterium | No | Yes | No | No | No |
| Caulobacter | No | Yes | Yes | No | No |
| Cellulomonas | Yes | No | No | No | Yes |
| Chromobacterium | Yes | No | No | No | Yes |
| Chromohalobacter | No | No | Yes | No | No |
| Chryseobacterium | No | No | No | Yes | No |
| Citrobacter | Yes | No | No | Yes | No |
| Colwellia | No | No | Yes | Yes | No |
| Comamonas | No | No | No | No | Yes |

TABLE 13-continued

Source genera for 16S rRNA sequences included in five 16S gene pools. Randomly drawn sequences from these pools were used in generation of mock datasets.

| | | | | | |
|---|---|---|---|---|---|
| Corallococcus | No | Yes | No | Yes | No |
| Corynebacterium | No | No | No | No | Yes |
| Cronobacter | Yes | No | No | Yes | No |
| Curtobacterium | Yes | No | No | Yes | Yes |
| Deinococcus | No | Yes | Yes | No | Yes |
| Delftia | No | No | Yes | No | Yes |
| Desulfosporosinus | Yes | No | No | Yes | No |
| Desulfotomaculum | No | No | Yes | Yes | No |
| Edwardsiella | No | No | Yes | Yes | No |
| Enterococcus | No | Yes | No | No | Yes |
| Erythrobacter | Yes | No | No | No | Yes |
| Eubacterium | No | No | Yes | No | No |
| Exiguobacterium | No | Yes | No | No | No |
| Flavobacterium | Yes | Yes | No | Yes | No |
| Francisella | Yes | Yes | No | No | No |
| Fusobacterium | No | No | No | No | Yes |
| Gallibacterium | No | No | Yes | No | No |
| Geobacillus | No | No | Yes | Yes | No |
| Glaciecola | No | No | No | Yes | Yes |
| Gluconobacter | No | Yes | No | No | No |
| Haemophilus | No | Yes | No | No | No |
| Halobacillus | No | No | No | Yes | No |
| Halomonas | No | Yes | No | Yes | Yes |
| Helicobacter | Yes | No | No | No | No |
| Herbaspirillum | No | No | No | Yes | No |
| Hydrogenophaga | No | No | Yes | No | No |
| Idiomarina | No | No | No | Yes | No |
| Kitasatospora | No | Yes | No | No | No |
| Klebsiella | Yes | No | No | No | No |
| Kocuria | No | No | Yes | No | No |
| Komagataeibacter | No | No | No | No | Yes |
| Lactobacillus | No | No | Yes | No | Yes |
| Lactococcus | Yes | No | No | Yes | No |
| Legionella | No | Yes | No | No | No |
| Leifsonia | No | Yes | No | No | Yes |
| Leptospira | No | Yes | No | No | No |
| Leucobacter | No | Yes | Yes | No | Yes |
| Leuconostoc | Yes | Yes | No | Yes | No |
| Listeria | Yes | No | No | No | No |
| Loktanella | No | Yes | Yes | No | No |
| Lysinibacillus | Yes | No | No | No | No |
| Lysobacter | No | No | No | No | Yes |
| Marinobacter | No | Yes | No | No | Yes |
| Marinobacterium | No | No | Yes | No | No |
| Marinomonas | No | No | No | Yes | Yes |
| Massilia | Yes | No | Yes | Yes | No |
| Methylobacterium | No | No | No | Yes | Yes |
| Microbispora | Yes | No | No | No | No |
| Micromonospora | Yes | Yes | No | No | No |
| Moraxella | No | No | Yes | No | No |
| Moritella | No | No | No | No | Yes |
| Mycoplasma | No | Yes | No | No | No |
| Neisseria | Yes | Yes | No | No | Yes |
| Nitrosomonas | No | No | Yes | No | No |
| Nocardioides | Yes | Yes | No | Yes | No |
| Novosphingobium | Yes | No | Yes | No | No |
| Oceanobacillus | Yes | No | Yes | Yes | No |
| Paenibacillus | Yes | Yes | No | Yes | No |
| Pandoraea | No | No | No | Yes | No |
| Pantoea | No | No | No | Yes | Yes |
| Paracoccus | No | No | No | No | Yes |
| Pectobacterium | No | No | Yes | No | Yes |
| Pediococcus | No | No | No | No | Yes |
| Photobacterium | No | No | Yes | No | Yes |
| Photorhabdus | No | Yes | Yes | No | No |
| Phyllobacterium | No | Yes | No | No | No |
| Planococcus | No | No | No | Yes | No |
| Polaribacter | No | No | Yes | No | No |
| Polynucleobacter | Yes | No | No | No | No |
| Proteus | Yes | No | Yes | No | No |
| Pseudomonas | No | No | No | No | Yes |
| Pseudoxanthomonas | No | Yes | No | No | No |
| Psychrobacter | No | No | Yes | No | No |
| Rahnella | Yes | No | No | No | No |
| Ralstonia | No | No | Yes | Yes | No |
| Rhizobium | No | Yes | Yes | No | Yes |

TABLE 13-continued

Source genera for 16S rRNA sequences included in five 16S gene pools. Randomly drawn sequences from these pools were used in generation of mock datasets.

| | | | | | |
|---|---|---|---|---|---|
| Rhodopirellula | No | Yes | Yes | Yes | Yes |
| Rickettsia | No | No | Yes | Yes | No |
| Ruegeria | No | No | No | No | Yes |
| Ruminococcus | No | Yes | No | No | No |
| Salmonella | No | Yes | No | Yes | Yes |
| Selenomonas | No | No | Yes | No | No |
| Serratia | No | Yes | No | Yes | No |
| Shewanella | Yes | No | No | No | Yes |
| Sorangium | Yes | No | Yes | No | No |
| Sphingobium | No | Yes | No | Yes | Yes |
| Spiroplasma | Yes | No | No | No | No |
| Sporolactobacillus | No | No | Yes | Yes | No |
| Staphylococcus | No | Yes | No | Yes | Yes |
| Stenotrophomonas | Yes | Yes | No | Yes | No |
| Streptococcus | No | Yes | No | No | No |
| Streptomyces | No | Yes | Yes | No | No |
| Streptosporangium | No | No | No | No | Yes |
| Taylorella | Yes | Yes | No | No | No |
| Thalassospira | No | Yes | Yes | No | No |
| Thermoanaerobacter | Yes | No | Yes | No | No |
| Thermoanaerobacterium | No | No | No | Yes | No |
| Thermus | No | No | No | Yes | No |
| Thiomonas | Yes | No | Yes | No | No |
| Trueperella | No | Yes | No | Yes | Yes |
| Vibrio | Yes | No | No | No | Yes |
| Virgibacillus | Yes | No | Yes | No | No |
| Weissella | No | Yes | No | No | Yes |
| Xanthomonas | No | Yes | No | Yes | No |
| Xenorhabdus | Yes | No | No | Yes | No |
| Xylella | No | Yes | No | No | No |

To obtain reads for building the mock metagenomic datasets corresponding to these pools, each time 10,000 16S rRNA genes were drawn randomly from a gene pool, such that the proportion of 16S rRNA genes drawn from any of the organisms are also randomized. 5 such datasets (with 10,000 reads each) corresponding to each of the 5 gene pools (a total of 25 mock datasets) were constructed for comparative evaluation. Different contiguous as well as non-contiguous combinations of V-regions were subsequently extracted from each of the 16S rRNA genes belonging to these mock datasets, and subjected to taxonomic analysis using Wang classifier, following the classification methodology described above. Taxonomic abundance values (obtained using different combinations of V-regions) were averaged over 5 mock datasets pertaining to the same gene pool. The averaged abundance values for each of the mock gene pools were compared against each other and the pre-annotated taxonomic attributes of their source (full-length) 16S rRNA genes, to assess the utility of the chosen combinations of V-regions. The results, in terms of classification accuracy at the species level, are depicted in Table 12. It was interesting to note that 18 out of the 20 combinations of V-regions, which could provide classification accuracy >=60% on average, constituted of non-contiguous V-regions. The best performing combination of adjacent V-regions was V2-V3, which on average provided 69.1% classification accuracy. In comparison, the combination of the non-contiguously placed V-regions V1+V4 demonstrated a high average classification accuracy of 77.2%.

Nine more simulated microbiomes mimicking different environmental and host associated niches—namely, gut, skin, vaginal, sub-gingival (oral), sputum (oral), nematode gut, soil, and aquatic were also generated. Taxonomic abundance estimates for eight of these environmental microbiomes were derived from datasets used in an earlier in silico study evaluating functional potential of diverse metagenomes Taxonomic abundance estimates for the aquatic microbiome was derived from a recent study. To populate these simulated microbiomes, sequences from RDP database were randomly drawn, while making sure that the proportions of 16S rRNA genes drawn from different genera were roughly similar to the proportions observed earlier for these environments. The taxonomic classification efficiency of the V-region combinations (at the species level) was also assessed on this set of simulated microbiome. The efficiency of the proposed non-contiguous combination of V-regions was further tested on nine additional simulated metagenomes mimicking different environmental and host associated niches as shown in Table 14. The data in the Table 14 have been collected from various sources in the art.

TABLE 14

Summary of datasets used for deriving taxonomic profiles pertaining to various environmental and host associated niches used togenerate simulated metagenomes mimicking the respective environments. Genera level abundances, averaged over all datasets pertaining to an environment, were used to draw respective proportions 16S rRNA genes from the set of downloaded RDP sequences while constructing the simulated metagenomics datasets

| Sample Identifier | Environment | No. of Samples |
|---|---|---|
| Gut1 (Prebiotics) | Gut(Human) | 283 |
| Gut2 (HMP) | Gut (Human) | 306 |
| Sputum | Oral Cavity (Human) | 68 |
| Skin | Skin (Human) | 149 |
| Sub-gingival | Oral Cavity (Human) | 91 |
| Vaginal | Vagina (Human) | 394 |
| Soil | Soil | 18 |
| Nematode | Nematode Gut (*Litoditis Marina*) | 36 |
| Aquatic | Aquatic | 20 |

Results pertaining to the human associated simulated metagenomes, namely, gut, skin, vaginal, subgingival (oral) and sputum (oral) are depicted in FIG. 4. It was interesting to note that optimal classification of reads from the simulated metagenomes pertaining to different niches could be obtained with different combinations of non-contiguous V-regions.

The combination of V1+V4 regions provided the maximum accuracy of classification for skin (60.2%) and one of the gut (86.0%) metagenomes (GUT2), whereas metagenomes pertaining to vaginal and sub-gingival niches were best resolved by the combination V1+V9 (with accuracies of 83.3% and 78.6% respectively). Optimal classification of sputum metagenomic samples (72.1%) could be obtained by another non-contiguous combination, viz. V1+V5 regions, which could also provide relatively more accurate classification for the GUT1 metagenome (82.5%). These results further reiterate the need of choosing an optimal combination of V-regions, preferably non-contiguous, for a specific sampled environment.

It was also noted that the high variability in taxonomic classification accuracies of individual V-region combinations while classifying samples pertaining to different environments. For example, while the combination V2+V4 could classify one of the gut microbiomes (Gut2) with 85.93% accuracy, the classification results were not as high when the same combination was used to classify the aquatic microbiome (69.2%). On the other hand, the combination V2+V7 was observed to provide decent classification for the simulated aquatic microbiome (72.8%), while performing not so well for the simulated gut microbiome datasets (65.8% for Gut1 and 70.9% for Gut2). These results further reiterate the need of choosing an optimal combination of V-regions, preferably non-contiguous, for a specific sampled environment.

It may be noted here that the paired-end reads generated for in silico evaluation of the utility of different combinations of V-regions were based on HMMs pertaining to the flanking constant regions, as provided by the V-xtractor program. Actual primer design may not always allow generation of reads identical to the in silico experiment, and results from a sequencing experiment may slightly vary from the validation results presented. A comparison of the paired-end reads generated in the in silico experiments with respect to those which may be obtained by using different sets of primers currently available for 16S rRNA amplicon sequencing as shown in FIG. 10.

It may be mentioned here that assessment of primer specificity on all sequences from RDP database (a total of 232,163 sequences having length >=1,200 bp) revealed that the combinations/pairs (either contiguous or non-contiguous) involving the V1-region could potentially amplify a lower fraction of sequences compared to other combinations. Apparently, the fraction of sequences that can be amplified by the said combinations is limited by the specificity/universality of the primer for V1-region. The presence of many incomplete/truncated SSU rRNA sequences in RDP database, which might be missing the V1 primer binding sites may also contribute to this observation. The overall results, however, do not indicate any significant deviations in the specificity (fraction of bacterial sequences amplified) of primer pairs targeting non-contiguous V-regions, when compared to the primers targeting contiguously placed V-regions.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for improving accuracy of taxonomic profiling of a microbial community based on amplicon sequencing, the method comprising:

collecting a biological sample from an environment;

obtaining a first subsample and a second subsample from the biological sample;

extracting microbial DNA from the first subsample and the second subsample;

sequencing, the extracted microbial DNA from the first subsample using a sequencer to get first DNA sequence data, wherein the first DNA sequence data comprises of a plurality of pairs of sequence fragments, wherein each pair of the plurality of pairs of sequence fragments is generated through paired-end sequencing of a first amplicon that comprises a first combination of informative regions within the first amplicon, wherein the first combination of informative regions comprises informative regions arranged contiguously or non-contiguously in a phylogenetic marker gene targeted in the first amplicon sequencing, the sequencing of the first combination of informative regions arranging contiguously comprising the steps of:

designing primers including a forward primer and a reverse primer against a stretch of the extracted microbial DNA such that the informative regions reside within the stretch and the primers target two contiguous informative regions, wherein the two contiguous informative regions are two adjacent informative regions;

generating paired-end reads including a forward read and a reverse read by performing the paired-end sequencing of the first amplicon, wherein the paired-end sequencing is a 250 bpx2 paired-end sequencing where the stretch of the extracted microbial DNA is sequenced from both ends; and merging the forward read and the reverse read into a single sequence forming a merged read based on an overlap between the forward read and the reverse read constituting a pair, wherein the overlap is found between the forward and the reverse read on sequencing the two adjacent informative regions; and wherein the informative regions contain phylogenetically relevant information;

sequencing, the extracted DNA from the second subsample using the sequencer to get second DNA sequence data, wherein the second DNA sequence data comprises of a plurality of pairs of sequence fragments, wherein each pair of the plurality of pairs of sequence fragments is generated through paired-end sequencing of a second amplicon that comprises a second combination of informative regions within the second amplicon, wherein the second combination of informative regions comprises informative regions arranged non-contiguously in the phylogenetic marker gene targeted in the second amplicon sequencing, the sequencing of the second combination of informative regions arranging non-contiguously comprising the steps of:

designing primers including aforward primer and areverse primer against a stretch of the extracted microbial DNA such that the informative regions reside within the stretch and the primers target two non-contiguous informative regions, wherein the two non-contiguous informative regions are two distantly separated informative regions;

generating paired-end reads including a forward read and a reverse read by performing the paired-end sequencing of the second amplicon, wherein the paired-end sequencing is a 250 bpx2 paired-end sequencing where the stretch of the extracted microbial DNA is sequenced from both ends;

concatenating the forward read and the reverse read into a single sequence forming a concatenated read using a string of multiple ambiguous nucleotide characters when the forward read and the reverse read do not overlap, wherein the overlap is not found between the forward read and the reverse read on sequencing the two separated informative regions;

wherein utility of targeting pairs of non-contiguously placed informative regions improves taxonomic classification accuracy, wherein the second combination of informative regions are different from the first combination of informative regions and one of the informative regions in the first combination of informative regions and the second combination of informative regions is shared by the first combination of informative regions and the second combination of informative regions, and wherein the first and second amplicon sequencing experiments target the phylogenetic marker gene;

generating, via one or more hardware processors, a first microbial taxonomic abundance profile of the first sequenced subsample by performing a taxonomic classification of phylogenetically relevant information corresponding to the first combination of informative regions, wherein the first combination of informative regions are submitted as query sequences for performing the taxonomic classification, and wherein the first microbial taxonomic abundance profile comprises abundance values corresponding to one or more pair of sequence fragments comprising the first combination of informative regions classified into a plurality of taxonomic groups;

generating, via the one or more hardware processors, a second microbial taxonomic abundance profile of the second sequenced subsample by performing the taxonomic classification of phylogenetically relevant information corresponding to the second combination of informative regions, wherein the second combination of informative regions are submitted as query sequences for performing the taxonomic classification, and wherein the second microbial taxonomic abundance profile comprises abundance values corresponding to one or more pair of sequence fragments comprising the second combination of informative regions classified into the plurality of taxonomic groups;

pre-computing, via the one or more hardware processors, taxonomic classification accuracies for various possible combinations of informative regions for microbes belonging to the plurality of taxonomic groups, wherein the pre-computing is based on marker gene sequences of known taxonomic origin present in existing sequence databases, to generate a computation table; and combining, via the one or more hardware processors, the first microbial taxonomic abundance profile and the second microbial taxonomic abundance profile of the first and the second sequenced subsample based on the computation table to generate a combined microbial taxonomic abundance profile, wherein combining the first microbial taxonomic abundance profile and the second microbial taxonomic abundance profile utilizes a combinatorial strategy and the combined microbial taxonomic abundance profile has a refined abundance value for each taxonomic group and has improved taxonomic classification accuracy as compared to the first microbial taxonomic abundance profile and the second microbial taxonomic abundance profile obtained individually for the first and the second subsample, targeting the first combination of informative regions and the second combination of informative regions in the phylogenetic marker gene, wherein the combinatorial strategy comprises:

obtaining the abundance values of a particular taxonomic group 'i' ($T_i^x$ and $T_i^y$) corresponding to the first and second sequenced subsamples, generated by performing the taxonomic classification utilizing the first combination of informative regions and the second combination of informative regions;

providing pre-computed relative accuracies $W_i^x$ and $W_i^y$ in taxonomic classification for the particular taxonomic group 'i' using the first combination of informative regions 'x' and the second combination of informative regions 'y'; and calculating the refined abundance value ($T_i^{xy}$) for the particular taxonomic group 'i ' using the following formula:

$$T_i^{xy} = \frac{\left(\frac{W_i^x}{W_i^y} * T_i^x\right) + T_i^y}{1 + \frac{W_i^x}{W_i^y}}$$

and calculating the refined abundance value for all the taxonomic groups to obtain a more accurate microbial taxonomic abundance profile as compared to the first microbial taxonomic abundance profile and the second microbial taxonomic abundance profile obtained individually for the first and the second subsample.

2. The method of claim 1, wherein the sequencing the extracted microbial DNA from the first subsample and the second subsample is performed on the first amplicon and the second amplicon, wherein the first amplicon and the second amplicon constitute a 16S rRNA gene or portions of the 16S rRNA gene, and wherein the 16S rRNA gene comprises multiple phylogenetically informative regions.

3. The method of claim 1, wherein each informative region of the first combination of informative regions and the second combination of informative regions is a variable region in a 16S rRNA gene amplicon.

4. The method of claim 1, wherein the choice of the phylogenetic marker gene and the first combination of informative regions and the second combination of informative regions within the marker gene selected for amplicon sequencing is based on the pre-computed taxonomic classification accuracies for the various possible combinations of informative regions for microbes belonging to the plurality of taxonomic groups.

* * * * *

SEQUENCE LISTING

```
<160> NUMBER OF SEQ ID NOS: 11

<210> SEQ ID NO 1
<211> LENGTH: 20
<212> TYPE: DNA
<213> ORGANISM: Artificial sequence
<220> FEATURE:
<223> OTHER INFORMATION: Primer for amplicon sequencing
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t

<400> SEQUENCE: 1

tnanacatgc aagtcgrrcg                                                   20


<210> SEQ ID NO 2
<211> LENGTH: 20
<212> TYPE: DNA
<213> ORGANISM: Artificial sequence
<220> FEATURE:
<223> OTHER INFORMATION: Primer for amplicon sequencing

<400> SEQUENCE: 2

agtggcggac gggtgagtaa                                                   20


<210> SEQ ID NO 3
<211> LENGTH: 19
<212> TYPE: DNA
<213> ORGANISM: Artificial sequence
<220> FEATURE:
<223> OTHER INFORMATION: Primer for amplicon sequencing

<400> SEQUENCE: 3

ggaggcagca gtrrggaat                                                    19


<210> SEQ ID NO 4
<211> LENGTH: 15
<212> TYPE: DNA
<213> ORGANISM: Artificial sequence
<220> FEATURE:
<223> OTHER INFORMATION: Primer for amplicon sequencing

<400> SEQUENCE: 4

agggtatcta atcct                                                        15


<210> SEQ ID NO 5
<211> LENGTH: 15
<212> TYPE: DNA
<213> ORGANISM: Artificial sequence
<220> FEATURE:
<223> OTHER INFORMATION: Primer for amplicon sequencing

<400> SEQUENCE: 5
```

accgcggckg ctggc 15

<210> SEQ ID NO 6
<211> LENGTH: 17
<212> TYPE: DNA
<213> ORGANISM: Artificial sequence
<220> FEATURE:
<223> OTHER INFORMATION: Primer for amplicon sequencing

<400> SEQUENCE: 6
cggtgtgtac aagaccc 17

<210> SEQ ID NO 7
<211> LENGTH: 19
<212> TYPE: DNA
<213> ORGANISM: Artificial sequence
<220> FEATURE:
<223> OTHER INFORMATION: Primer for amplicon sequencing

<400> SEQUENCE: 7
cgtcatccmc accttcctc 19

<210> SEQ ID NO 8
<211> LENGTH: 17
<212> TYPE: DNA
<213> ORGANISM: Artificial sequence
<220> FEATURE:
<223> OTHER INFORMATION: Primer for amplicon sequencing

<400> SEQUENCE: 8
crrcacgagc tgacgac 17

<210> SEQ ID NO 9
<211> LENGTH: 18
<212> TYPE: DNA
<213> ORGANISM: Artificial sequence
<220> FEATURE:
<223> OTHER INFORMATION: Primer for amplicon sequencing

<400> SEQUENCE: 9
cgtcaattcm tttgagtt 18

<210> SEQ ID NO 10
<211> LENGTH: 16
<212> TYPE: DNA
<213> ORGANISM: Artificial sequence
<220> FEATURE:
<223> OTHER INFORMATION: Primer for amplicon sequencing

<400> SEQUENCE: 10
gacgggcggt gtgtrc 16

<210> SEQ ID NO 11
<211> LENGTH: 19
<212> TYPE: DNA
<213> ORGANISM: Artificial sequence
<220> FEATURE:
<223> OTHER INFORMATION: Primer for amplicon sequencing

<400> SEQUENCE: 11
tgctgcctcc cgtaggagt 19